United States Patent [19]

Botchner

[11] Patent Number: 5,541,082
[45] Date of Patent: Jul. 30, 1996

[54] MICROBIOLOGICAL MEDIUM

[75] Inventor: Barry Botchner, Alameda, Calif.

[73] Assignee: Biolog, Inc., Hayward, Calif.

[21] Appl. No.: 450,935

[22] Filed: May 25, 1995

Related U.S. Application Data

[62] Division of Ser. No. 236,324, Apr. 29, 1994, Pat. No. 5,464,755.

[51] Int. Cl.$^6$ .................. C12Q 1/00; C12Q 1/02; C12Q 1/04

[52] U.S. Cl. .................. 435/34; 435/243

[58] Field of Search .................. 435/34, 243

[56] References Cited

U.S. PATENT DOCUMENTS

| | | | |
|---|---|---|---|
| 3,496,066 | 2/1970 | Berger et al. | 195/103.5 |
| 3,634,198 | 1/1972 | Trahan | 195/100 |
| 3,870,601 | 3/1975 | Warren et al. | 195/103.5 R |
| 3,936,356 | 2/1976 | Janin | 195/103.5 R |
| 3,957,584 | 5/1976 | Kronish et al. | 195/103.5 R |
| 4,241,186 | 12/1980 | Roth | 435/243 |
| 4,282,317 | 8/1981 | Roth | 435/34 |
| 4,351,823 | 9/1982 | Rubin | 424/9 |
| 4,556,636 | 12/1985 | Belly et al. | 435/34 |
| 4,591,554 | 5/1986 | Koumura et al. | 435/18 |
| 4,603,108 | 7/1986 | Bascomb | 435/34 |
| 4,673,638 | 6/1987 | Grosch et al. | 435/34 |
| 4,849,342 | 7/1989 | Ben-Michael | 435/7 |
| 4,886,760 | 12/1989 | Ben-Michael | 436/66 |
| 5,098,832 | 3/1992 | Rambach | 435/34 |
| 5,134,063 | 7/1992 | Bochner | 435/29 |
| 5,182,082 | 1/1993 | Monthony et al. | 422/57 |
| 5,194,374 | 3/1993 | Rambach | 435/34 |
| 5,210,022 | 5/1993 | Roth et al. | 435/34 |
| 5,238,817 | 8/1993 | Bobrow et al. | 435/28 |

OTHER PUBLICATIONS

Baron & Finegold, *Diagnostic Microbiology*, 8th ed., C. V. Mosby, (1990), pp. 37, 253–262.

Clarridge et al., "Laboratory Diagnosis of Urinary Tract Infections," Cumitech 2A, pp. 1–15, American Society for Microbiology, (1987).

Koneman et al., *Color Atlas and Textbook of Diagnostic Microbiology*, pp. 79–80, J. B. Lippincott Co. (1992).

Power & McCuen, *Manual of BBL® Products and Laboratory Procedures*, 6th ed., pp. 10–49, Becton Dickinson Microbiology Systems (1988).

M. Pezzlo, "Detection of Urinary Tract Infections by Rapid Methods," Clin. Microbiol. Rev., 1:268–280 (1988).

C. M. Kunin, *Detection, Prevention and Management of Urinary Tract Infections*, p. 92, Lea & Febiger (1979).

Y. Yee et al., "Further evidence associating hemolytic uremic syndrome with infection by verotoxin–producing *Escherichia coli* O157:H7," J. Infect. Dis., 154:522–524 (1986).

S. Falkow and J. Mekalanos, "The Enteric Bacilli and Vibrios," pp. 561–587 in B. D. Davis et al. (eds.), *Microbiology*, 4th ed., J. B. Lippincott Co., Philadelphia (1990).

J. J. Farmer et al., "Biochemical Identification of New Species and Biogroups of *Enterbacteriaceae* Isolated form Clincal Specimens," J. Clin. Microbiol., 21:46–76 (1985).

W. K. Joklik et al., *Zinsser Microbiology*, pp. 631–636, Appleton–Century–Crofts, Norwalk, CT (1984).

R. C. Moellering, "The Enterococcus: A versatile pathogen," pp. 3–6, in *Challenges in Gram–Positive Infection: A Global Perspective*™, Healthmark (1988).

R. H. Latham et al., "Urinary tract infections in young adult women caused by *Staphylococcus saprophyticus*," J. Amer. Med. Assoc., 250:3063–3066 (1983).

G. Wallmark et al., "*Staphylococcus saprophyticus*: A Frequent Cause of Urinary Tract Infection Among Female Outpatients," J. Infect. Dis., 138:791–797 (1978).

B. Hovelius and Måardh, "Staphylococcus Saprophyticus As a Common Cause of Urinary Tract Infections," Rev. Infect. Dis., 6:328–337 (1984).

W. Lee et al., "Pyelonephritis and sepsis due to *Staphylococcus saprophyticus*," J. Infect. Dis., 155:1079–1080 (1987).

A. J. Schaeffer, "Cystitis and Pyelonephritis," pp. 418–435, in Youmans et al., (eds.), *The Biologic and Clincal Basis of Infectious Disease*, W. B. Saunders, (1986).

De Montclos & Carret, "Optimisation de l'examen cytobacteriolique urinaire," Spectra Biologic, 92:49–53 (1992).

Heizmann et al., "Rapid Identification of *Escherichia coli* by fluorocult media and psoitive indole reaction," J. Clin. Microbiol., 26:2682–2684 (1988).

Orenga et al., "Urinary Tract Infections: Improved CPS ID, a New Ready–to–Use Medium for Enumeration and Identification of *Escherichia coli*, *Proteeae* and *Enterococcus*," Rapid Methods and Automation in Microbiology and Immunology, London, Sep. (1993).

Orenga et al., "Urinary Tract Infections: Improved CPS ID, a New Ready–to–Use Medium for Enumeration and Identification of *Escherichia coli*, *Proteeae* and *Enterococcus*," Abstr. P14/2, p. 107, Abstracts of Seventh International Congress on Rapid Methods and Automation in Microbiology and Immunology, London (12–15 Sep. 1993).

Freydiere and Gille, "A New CPS Medium for Rapid Identification and Enumeration of Bacteria in Urine Sample", Abstract P14/5, p. 107, Abstracts, Seventh International Congress on Rapid Methods and Automation in Microbiology and Immunology, London (12–15 Sep. 1993).

"Technical Information: Uropath II Quad TI No. 2485–A," Remel, Lenexa, Kansas (1989).

"Technical Information: Urinary Quad (dextrose/citrate/EMB/urea) TI No. 2480–A," Remel, Lenexa, Kansas (1989).

(List continued on next page.)

*Primary Examiner*—Carolyn Paden
*Attorney, Agent, or Firm*—Medlen & Carroll

[57] ABSTRACT

The present invention is directed to methods and media for the isolation and presumptive identification of various bacteria. In particular, the organisms commonly associated with urinary tract infections are distinguished based on their colonial morphology and color.

20 Claims, No Drawings

OTHER PUBLICATIONS

Fisher Scientific Catlog, 1993/1994, at pp. 634–636.

Yamada et al., "Comparative immunological studies on arylsulfatse in bacteria of the family *Enterobacteriaceae*: Occurrence of latent arylsulfatase protein regulated by sulfur compounds and tyramine," J. Bacteriol., 133:536–541 (1978).

Brown and Foster, "A simple diagnostic milk medium for *Pseudomonas aeruginosa*", J. Clin. Pathol., 23:172–177 (1970).

R. R. Facklam and J. A. Washington, III, "Streptococcus and related catalase–negative gram–positive cocci," in A. Balows et al. (eds.), *Manual of Clinical Microbiology*, American Society for Microbiology, pp. 238–257, 652–656 (1991).

E. O. King et al., "Two Simple Media for the Demonstration of Pyocyanin and Fluorescein," J. Lab & Clin. Med., 44:301–307 (1954).

J. F. MacFaddin, *Media for Isolation–Cultivation–Maintenance of Medical Bacteria*, pp. 652–656, 821–827, Williams & Wilkins (1985).

T. Harada and Y. Murooka, "Participation of tyramine oxidase in multiple control of bacterial arylsulfatase synthesis," Mem. Inst. Sci. Ind. Res., Osaka Univ., 37:45–58 (1980).

M. Rosenberg et al., "Initial testing of a novel urine culture device," J. Clin. Microbiol., 30:2686–2691 (1992).

J. L. Sepulveda, "Rapid presumptive identification of gram–negative rods directly form blood cultures by simple enzymatic tests," J. Clin. Microbiol., 28:177–181 (1990).

A–M Freydiere and Y. Gille, "Detection of salmonellae by using Rambach agar and by a C8 esterase spot test," J. Clin. Microbiol., 29:2357–2359 (1991).

T. D. Bevis, "A modified electrolyte deficient culture medium," J. Med. Lab Technol. 25:38–41 (1986).

G. L. Delisle and A Lay, "Rapid Detection of Escherichia coli in urine samples by a new chromogenic β–glucuronidase assay," J. Clin. Microbiol. 27:778–779 (1989).

M. P. Friedman et al., "Rapid isolation and presumptive diagnosis of uropathogens by using membrane filtration and differential media," J. Clin. Microbio. 29:2385–2389 (1991).

E. W. Frampton and L. Restaino, "Methods for *Escherichia coli* identification in food, water and clinical samples based on beta–glucuronidase detection," J. Applied Bacteriology 74:223–233 (1993).

R. Gruenewald et al., "Use of Rambach propylene glycol containing agar for identification of *Salmonell spp.*," J. Clin. Microbiol. 29:2354–2356 (1991).

P. M. Hawkey et al., "Selective and differential medium for the primary isolation of members of the *Proteeae*," J. Clin. Microbiol. 23:600–603 (1986).

M. Manafi et al., "Fluorogenic and chromogenic substrates used in bacterial diagnostics," Microbiological Reviews 55:335–348 (1991).

W. Hansen and E. Yourassowsky, "Detection of β–glucuronidase in lactose–fermenting members of the family *Enterobacteriaceae* and its prensence in bacterial urine cultures," J. Clin. Microbiol. 20:1177–1179 (1984).

J. L. Sepulveda et al., "Rapid presumptive identification of gram–negative rods directly from blood cultures by simple enzymatic tests," J. Clin. Microbiol. 28:177–181 (1990).

M. C. Thaller et al., "Modified MacConkey medium which allows simple and reliable identification of *Providencia stuartii*," J. Clin. Micorbiol. 30:2054–2057 (1992).

W. D. Watkins et al., "Novel compound for identifying *Escherichia coli*," Appl. Env. Microbiology 54:1874–1875 (1988).

P. Kampfer, "Differentiation of *Corynebacterium spp., Listeria spp.*, and related organisms by using fluorogenic substrates," J. Clin. Microbiol. 30:1067–1071 (1992).

P. Kampfer et al., "Fluorogenic substrates for differentiation of gram–negative nonfermentative and oxidase–positive fermentative bacteria," J. Clin. Microbiol. 30:1402–1406 (1992).

M. Olsson et al., "Identification of Salmonellae with 4–methylumbelliferyl caprolate fluorescence test," J. Clin. Microbiol. 29:2631–2632 (1991).

A. Rambach, "New plate medium for facilitated differentiation of Slamonelle spp. from Proteus spp. and other enteric bacteria," Appl. Env. Microbiol. 56:301–303 (1990).

R. M. Atlas (L. C. Parks, ed.), "*Handbook of Microbiological media*," pp. 196, 587, 601, 630, 810, 840, CRC Press, Boca Raton, Fla. (1993).

R. Pompei et al., "Patterns of phosphatase activity among enterobacterial species," Intl. J. Systematic Bacteriology 43:174–178 (1993).

F. Soriano and C. Ponte, "Letter to the editor: Processing urine specimens: Overnight versus two–day incubation," J. Clin. Microbiol. 30:3033–3034 (1992).

"Rambach® agar for identification of Salmonella in foodstuffs and clinical specimen," BDH Facts, Apr. (1992).

J. F. MacFaddin, *Media for Isolation–Cultivation–Identification–Maintenance of Medical Bacteria*, pp. 209–212, 471–478, Williams & Wilkins (1985).

M. J. Henderson and F. H. Milazzo, "Arylsulfatase in *Salmonella typhimurium*: Detection and influence of carbon source and tyramine on its synthesis," J. Bacteriology 139:80–87 (1979).

P. Goullet and B. Picard, "Characterization of enterobacteria by esterase specific–activity profiles," J. Gen. micrbiol. 136:431–440 (1990).

H. Dusch and M. Atlwegg, "Comparison of Rambach agar, SM–ID medium, and hektoen enteric agar for primary isolation of non–typhi *Salmonella* from stool samples," J. Clin. Microbiol. 31:410–412 (1993).

S. F. Dealler et al., "Enzymatic degradation of urinary indoxyl sulfate by *Providencia stuartii* and *Klebsiella pneumonia* causes purple urine bag syndrome," J. Clin. Microbiol. 26:2152–2156 (1988).

W. R. Heizamann, "Rapid methods and computer assisted diagnosis in medical microbiology," Acta Microbiologica Hungarica 38:305–313 (1991).

G. H. Sandys, "A new method of preventing swarming of *Proteus* sp. with a description of a new medium suitable for use in routine laboratory practice," pp. 224–233, *The Journal of Medical Laboratory Technology (1959)*.

L. V. Coates, "Purple serum agar," pp. 187–190, *The Journal of Medical Laboratory Technology (1954)*.

F. J. Hernandez et al., "Repair and enterotoxin synthesis by Staphylococcus aureus after thermal shock," Appl. Environ. Microbiol. 59:1515–1519 (1993).

P. R. Murray et al., "Clinical evaluation of three urine screening tests," J. Clin. Microbiol. 25:467–470 (1987).

J. Mackey and G. H. Sandys, "Diagnosis of urinary infections," British Med. Journal, 7 May 1173 (1966).B. A. Lipsky et al., "Comparison of the automicrobic system, acridine orange–stained smears, and gram–stained smears in detecting bacteriuria," J. Clin. Microbio. 22: 176–181 (1985).

P. Kramer et al., "Glycosidase profiles of members of the family *Enterobacteriaceae*," J. Clin. Microbiol. 29:2877–2879 (1991).

L. Jackson et al., "β–glucuronidase activies of fecal isolates from healthy swine," J. Clin. Microbiol. 30:2113–2117 (1992).

"Techincal information: Uropath II Quad TI No. 2485–A," Remel, Lenexa, Kansas (1989).

A. N. Ley et al., "Use of indoxyl–β–D–glucuronide for the enumeration of *Escherichia coli,*" Abstract Q–35, American Society for Microbiology Abstracts (1988).

G. Chang and R. Lum, "Tryptophan and glalctosidase media: Simple and specific ways to enumerate *Escherichia coli* and total coliforms in water and food," Abstract No. Q–12, American Society for Microbiology Abstracts (1990).

"Red–Gal tracks tagged clones: New histochemical stain colors marker genes red," vol. 1, Issue 1, pp. 1, 4, *The producers: News from Research Organics,*" Research Organics, Inc., Cleveland, Ohio (1992).

"The Oxoid manual of culture media, ingredients and other laboratory services," pp. 93, 96–98, 260, 261, Hampshire England (1982).

"Difco Manual: Dehydrated culture media and reagents for microbiology," pp. 546, 547, 940, 941, Difco Laboratories, Detroit, Mich. (1984).

G. W. Chang et al., "INDEC Medium: Omission of lactose from the US–EPA promulgated EC+MUG medium gives both an indole and an improved MUG test," Abstract N–47, p. 300, American Society for Microbiology Abstracts of the General Meeting (1992).

G. W. Chang and R. A. Lum, "Improved recovery of chlorine–injured *Escherichia coli* on acidified media," Abstract N–46, p. 299, American Society for Microbiology Abstracts of the General Meeting (1992).

P. I. Tarr et al., "*Escherichia coli* O157:H7 and the hemolytic uremic syndrome: Importance of early cultures in establishing the etiology," J. Inf. Dis. 162:553–556 (1990).

"Substrates and reagents," Biosynth AG, Switzerland (1992).

Diaslide—as easy to use as a book mark," Savyon Diagnostics Ltd., Israel (1992).

"Technical information: Urinary Quad (dextrose/citrate/EMB/urea) TI No. 2480–A," Remel, Lenexa, Kansas (1989).

"Bacteria & yeast identificaton test panels, " Biolog. Inc., Hayward, Calif. (1993).

Manafi et al. Microbiological Reviews vol. 55 No. 3 vol. 55 No. 3 pp. 335–348 (1991).

Brown et al. J Clin Path.

MICROBIOLOGICAL MEDIUM

This is a divisional of application Ser. No. 08/236,324 filed on Apr. 29, 1994 now U.S. Pat. No. 5,464,755.

FIELD OF THE INVENTION

The present invention relates to culture media useful for rapid screening of clinical cultures to detect some of the most common bacterial pathogens. The reactions observed on these media are useful for rapid and cost-effective presumptive diagnosis of infection due to various bacteria. Although many additional applications are contemplated, these media are particularly useful for testing urine samples.

BACKGROUND OF THE INVENTION

The diagnosis of infectious disease has traditionally relied upon microbiological culture methods to identify the causative organism and determine the appropriate antimicrobial treatment. This has remained so despite recent advances in molecular and immunological diagnostics. While the development of rapid and automated methods has served to increase the efficiency of microbiological analysis, traditional quantitative culture methods remain critical for definitive diagnosis of urinary tract and other infections (Baron & Finegold, *Diagnostic Microbiology*, 8th ed., C. V. Mosby, [1990], p. 253).

After proper specimen collection and transport, the laboratory professional must determine which of a multitude of culture media are most appropriate to use with the culture at hand. It is important to consider the type of specimen (e.g., urine, blood, sputum, etc.), and the most commonly isolated organisms associated with disease or infection at the site of specimen collection. The time and cost necessary to achieve a final diagnosis also must be borne in mind.

With respect to the type of specimen, there are considerations related to the normal flora from which the pathogens must be differentiated. This is particularly true for fecal, rectal, vaginal, buccal and other samples which commonly contain a characteristic background flora. Urine, a fluid which is normally sterile when excreted from the kidneys, often becomes contaminated with flora from the urethra, urethral opening and skin. Indeed, as voided, urine is by no means sterile. The first voided 10 ml volume of urine can contain up to $10^4$ organisms per ml, due to the dislodgement of bacteria from the urethra This necessitates the differentiation of normal flora contaminants from the infecting organism(s).

As with most body sites, the normal urethra supports a characteristic normal flora. In females, the organisms comprising the normal flora vary with age and health. In premenarchal females, 66% of the organisms are aerobic coryneforms, lactobacilli, and coagulase-negative staphylococci. Streptococci are often present also. In women of reproductive age, lactobacilli are the most common isolates (Clarridge et al., "Laboratory Diagnosis of Urinary Tract Infections," Cumitech 2A, p. 1, American Society for Microbiology, 1987). In post-menopausal women, there is a marked increase in the number of anaerobes, particularly *Bacteroides melaninogenicus* (Clarridge et al., p. 1 ). Other organisms, such as mycoplasmas and low densities of enteric gram-negative rods may also be recovered from the urethra of healthy women (Clarridge et al.).

In males, less indigenous flora is isolated from urine. Coagulase-negative staphylococci, enterococci (i.e., group D streptococci), coryneforms, and mycoplasmas may be isolated from the urethra and urine of healthy men (Clarridge et al., supra). Table 1, lists the commensal flora (i.e., normal flora) associated with the human urinary tract.

TABLE 1

Commensal Flora Associated With The Urinary Tract*
Resident Flora of the Urethra Coagulase-negative Staphylococci
Viridans and Non-Hemolytic Streptococci
Lactobaccilli
Corynebacterium sp. (diphtheroids)
Neisseria (non-pathogenic species)
Transient Gram-Negative Aerobes (including Enterobacteriaceae)
Anaerobic Cocci
Propionibacterium sp.
Anaerobic Gram-Negative Cocci and Bacilli
Commensal Mycobacterium sp.
Commensal Mycoplasma sp.
Occasional Yeasts

*Koneman et al., Color Atlas and Textbook of Diagnostic Microbiology, 4th edition, (p. 79) (J. B. Lippincott Co., 1992); Baron & Finegold, Diagnostic Microbiology, 8th ed., pp. 253–262 (C. V. Mosby, 1990); and Power & McCuen, Manual of BBL ® Products and Laboratory Procedures, 6th ed., pp. 48–49 (Becton Dickinson Microbiology Systems, 1988).

Because of the associated normal flora and the desire to identify pathogenic organisms, methods of urine collection have been developed which minimize the chances of contamination, including the clean-catch midstream sample, careful catheterization, suprapubic aspiration, bladder washout, and cystoscopy. In situations where the patient cannot or will not provide a clean-catch sample, suprapubic aspiration is the method of choice (e.g., infants).

Urinary tract infections (UTI's) are among the most common infections in humans. It has been estimated that approximately 20% of all women will experience at least one UTI, with the incidence increasing with age (Baron & Finegold, *Diagnostic Microbiology*, 8th ed., p. 254, (C. V. Mosby, 1990)). UTI diagnosis is among the most frequent clinical investigation, with infections of the urinary tract second in frequency only to upper respiratory infections. Indeed, the requests for bacteriuria detection far exceed those for respiratory pathogen detection (Pezzlo, "Detection of Urinary Tract Infections by Rapid Methods," Clin. Microbiol. Rev., 1:268 (1988)). Overall this represents a major cost to laboratories.

The risk of UTI's is significantly increased for patients with indwelling catheters, to the point where it is highly predictable that they will eventually develop at least one UTI. With the ever-increasing number of patients in hospitals and nursing homes with long-term indwelling urinary catheters, this represents a large patient population. Even short-term catheterization presents a significant risk as there is a 20% chance that hospitalized patients with short-term catheters will develop UTI's (Baron and Finegold, supra). Indeed, the National Nosocomial Infections Study (NNIS) conducted by the Centers for Disease Control (CDC) reported that 5% to 6% of all hospitalized patients acquire nosocomial infections. It is estimated that this extends the patient's hospital stay by about 3.2 days and adds approximately $1800 to the direct costs (in 1986 figures). This amount does not take into consideration such factors as physician charges, loss of productivity, and costs associated with deaths (at least 1% of nosocomially infected patients die as a direct result of their nosocomial infection and contribute to the deaths of an additional 2–3% of infected patients).

Most UTI's are acquired by contamination of the urinary tract with the patient's fecal matter. Thus, the members of the Enterobacteriaceae and other organisms present in the patient's gastrointestinal tract are responsible for the majority of UTI's, with *E. coli* causing the greatest number of infections. The establishment of the gastrointestinal tract as the usual reservoir for UTI's is supported by the observation that the distribution of *E. coli* serotypes in UTI's corresponds closely with their relative abundance in the affected patient's gut (C. M. Kunin, *Detection, Prevention and Management of Urinary Tract Infections*, Lea & Febiger ([1979], p. 92). Of particular significance is the association of certain *E. coli* strains with such serious diseases as hemolytic uremic syndrome (W. R. Gransden et al., "Further evidence associating hemolytic uremic syndrome with infection by verotoxin-producing *Escherichia coli* O157:H7," J. Infect. Dis., 154:522–534 [1986]), highlighting the importance of *E. coli* strains in severely debilitating UTI's.

In addition to *E. coli*, other members of the Enterobacteriaceae have been associated with UTI's. For example, Proteus is frequently isolated in UTI's in boys (Kunin, at pp. 47 and 92). *Klebsiella pneumoniae* is another important organism in urinary tract infections, as it has been reported to be the second most common pathogen isolated from UTI's (S. Falkow and J. Mekalanos, "The Enteric Bacilli and Vibrios," pp. 561–587 in B. D. Davis et al. (eds.), *Microbiology*, 4th ed., J. B. Lippincott Co., Philadelphia, 1990]). Indeed, of the Enterobacteriaceae, "80 to 95% of all isolates seen in a general hospital setting will be *Escherichia coli, Klebsiella pneumoniae*, or *Proteus mirabilis*." (J. J. Farmer et al., "Biochemical Identification of New Species and Biogroups of Enterobacteriaceae Isolated from Clinical Specimens," J. Clin. Microbiol., 21:46–76 [1985]). Undoubtedly, given the large number of specimens, a major proportion of these isolates are from UTI's. Other species of enteric bacteria are infrequently isolated from UTI's including such noted pathogens as Salmonella and Shigella.

*Pseudomonas aeruginosa*, an organism that is ubiquitous in the environment can infect almost any tissue or body site, including localized lesions in the urinary tract. UTI's due to *P. aeruginosa* are more common among the elderly (W. K. Joklik et al., *Zinsser Microbiology*, Appleton-Century-Crofts, Norwalk, Conn., 1984, p. 631–636). This organism is recognized as being particularly debilitating in patients with underlying disease or immunocompromised conditions.

In addition to the gram-negatives, various gram-positive organisms are commonly associated with UTI's. *Enterococcus faecalis* is a gram-positive coccus previously included within the genus Streptococcus. Like *E. coli* (and most species of Enterobacteriaceae), *E. faecalis* is a member of the normal gastrointestinal flora of humans and may also be found among the normal vaginal flora. Although *E. faecalis* is associated with various other diseases, UTI's are the most frequent diseases caused by this organism (R. C. Moellering, "The Enterococcus: A versatile pathogen," pp. 3–6, *in Challenges in Gram-Positive Injection: A Global Perspective*™, Healthmark [1988]). Treatment considerations are significant in *E. faecalis* disease, as this organism is resistant to a large number of antimicrobial agents. For example, *E. faecalis* is tolerant to a number of antimicrobials that are bactericidal against other bacteria. This high degree of antimicrobial resistance highlights the necessity of identifying this organism from UTI's.

Of the important gram-positive organisms, *S. saprophyticus* was relatively recently identified as a cause of UTI's (R. H. Latham et al., "Urinary tract infections in young adult women caused by *Staphylococcus saprophyticus*," J. Amer. Med. Assoc., 250:3063–3066 [1983]; and G. Wallmark et al., "*Staphylococcus saprophyticus:* A Frequent Came of Urinary Tract Infection Among Female Outpatients," J. Infect. Dis., 138:791–797 [1978]). Prior to the association of this organism with UTI's, it was generally thought that coagulase-negative staphylococci were apathogenic when isolated from the urinary tract (see e.g., B. Hovelius and M ardh, "Staphylococcus Saprophyticus As a Common Cause of Urinary Tract Infections," Rev. Infect. Dis., 6:328–337, 1984). As *S. saprophyticus* is one of the most common organisms associated with UTI's in young women, the importance of this organism is now recognized. Importantly, not only are these organisms associated with UTI's, they have also been associated with serious infections such as pyelonephritis and sepsis (W. Lee et al., "Pyelonephritis and sepsis due to *Staphylococcus saprophyticus,*" J. Infect. Dis., 155:1079–1080 [1987]). Unlike *E. coli* and the other enteric organisms, the reservoir for *S. saprophyticus* remains to be determined.

The organisms discussed above are most commonly associated with ascending infection (A. J. Schaeffer, "Cystitis and Pyelonephritis," pp. 418–435, in Youmans et al., (eds.), *The Biologic and Clinical Basis of Infectious Disease*, W. B. Saunders, [1986]). However, organisms may enter the urinary tract by direct extension from the gastrointestinal tract or through hematogenous spread. UTI's may also arise as infections secondary to bacteremia associated with extensive infection at other body sites (Sehaeffer, at pp. 421–423). Hematogenous spread to the kidneys is more common with organisms such as *Staphylococcus aureus*, Candida sp., and Mycobacterium sp. Thus, organisms may gain access to the structures of the urinary tract through a variety of means, including surgical procedures and catheterization.

The following table lists the organisms commonly associated with hospital and community-acquired UTI's. Notably, a large proportion of these organisms are also residents of the normal gastrointestinal and/or urinary tracts and/or vagina. Table 3 lists the organisms more rarely isolated from UTI's.

TABLE 2

Organisms Most Commonly Associated With UTI's Acquired In The Community and Hospital Settings

| | Outpatients | | Hospitalized Patients | |
|---|---|---|---|---|
| Organism | Initial Cases (%) | Recurrent Cases (%) | Medical Wards (%) | Intensive Care Units (%) |
| E. coli | ≧90 | 69 | 42 | 24 |
| P. mirabilis | 5 | 8 | 6 | 2 |
| Klebsiella-Enterobacter sp. | 1 | 6 | 13 | 16 |
| Enterococcus sp. | 1 | 3 | 15 | 23 |
| Staphylococcus sp. (coagulase negative) | 1 | 3 | 7 | 5 |
| P. aeruginosa | 0 | <1 | 6 | 17 |
| S. marcesens | 0 | 0 | 1 | 3 |
| All other organisms | 2 | 11 | 10 | 10 |

*After Clarridge et al., p. 2.

TABLE 3

Less Common And Unusual Agents Associated With Urinary Tract Infections*

Mycobacterium sp.
Leptospira sp.
*H. influenzae*
*G. vaginalis*
Acinetobacter sp.
Alcaligenes sp.
Pseudomonas sp.
Citrobacter sp.
*N. gonorrhoea*
Salmonella sp. (including S. typhi)
Shigella sp.
β-Hemolytic Streptococci
Anaerobes
*C. trachomatis*
*T. vaginalis*
*S. haematobium*
Herpes Virus

*Koneman et al.,; Baron & Finegold; and Power & McCuen.

Although many organisms may be isolated from UTI's, the chances are good that the isolate will belong to one of the organisms listed in Table 2, highlighting the importance of identifying a relatively small number of organisms associated with UTI's.

An additional concern relates to the type of cultures isolated from the urinary tract. Pure cultures are most commonly associated with UTI's in the general population. However, mixed cultures are frequently observed in hospitalized patients.

These mixed infections may present treatment problems, as the therapeutic regimen must be directed to all of the organisms involved. The frequency of mixed cultures is highlighted by a recent study cited by Orenga et al. (supra), in which De Montclos & Carret found that 25% of the urine cultures from hospitalized patients were mixed (De Montclos & Carret, "Optimisation de l'examen cytobacteriolique urinaire," Spectra Biologie, 92:49–53 (1992)). Importantly, mixed infections may also present diagnostic problems, as certain organisms may mask the presence of other species.

Due to the prevalence of UTI's, diagnosis of these infections is a common laboratory procedure. Various methods have been developed for the isolation, identification, and/or detection of the organisms most commonly associated with UTI's. Of these methods, there are two major categories: (1) culture methods, which utilize traditional microbiological culturing techniques to isolate, and then identify microorganisms based on their characteristic biochemical profiles, and for some species, their serological profiles; and (2) non-culture methods, which utilize various enzyme and other systems to detect the presence of infection.

I. Culture Methods for Diagnosis of Urinary Tract Infections

Currently, diagnosis of bacterial UTI's is generally accomplished by means of microbiological culturing and identification of organisms present in urine samples from infected patients. However, a majority of urine specimens submitted to clinical laboratories are negative or have bacterial colony counts below levels considered to be clinically significant (see e.g., Koneman et al.., at 256–257).

Historically, the number of organisms present in a urine sample has been considered to be an important factor in differentiating contaminated samples from those representing true UTI's. Thus, quantitation of the organisms present in a sample is often estimated.

Quantitation may be accomplished by pour plate methods which involve mixing dilutions of a sample with measured volumes of molten agar, pouring the mixture into petri plates, allowing the agar to solidify, incubating for approximately 24 hours, counting the number of colonies present in the plates, and then calculating the number of organisms present in the original sample (Power and McCuen, pp. 48–49; and Clarridge et at., p. 6). While pour plates provide a relatively reliable estimate of the number of organisms present in the sample, the time and manipulations necessary to perform the method make it impractical for use in the clinical setting (Clarridge et al., p. 6).

The method much more commonly used is a streak plate method, in which a calibrated loop designed to deliver a known volume (either 0.01 or 0.001 ml) of urine, is dipped into the sample and the inoculum present in the loop is streaked onto an agar plate (see e.g., E. J. Baron and S. M. Finegold, *Diagnostic Microbiology*, C. V. Mosby, St. Louis, 1990, pp. 253–262). Following incubation for 18–24 hours, the number of colonies is determined in order to provide an estimate of the number of organisms present in the patient's urine sample.

The commonly used standard is that a count of greater than 10,000 CFU (colony forming units)/ml indicates a UTI. However, the density of pathogens and contaminating organisms in a "positive" specimen may be as low as 100 CFU/ml. Thus, some practitioners identify all bacterial species in numbers greater than 100 CFU/ml, with the exception of normal skin or genital flora (Baron and Finegold, p. 258). A count greater than 1000 has been shown to be significant in males (Clarridge et al., p. 7).

If a specimen contains one or two strains growing in significant numbers, the strains are usually identified and the antimicrobial susceptibility patterns of the strains determined (Baron and Finegold, p. 260). Regardless of the colony count, a pure culture of *S. aureus* is considered significant (Baron and Finegold, p. 260). Usually, any yeasts isolated are identified to the genus and/or species level, and reported to the physician (Baron and Finegold, p. 260). The following table shows the counts associated with the presence or absence of infection related to the sample volume.

TABLE 4

Diagnosing Urinary Tract Infections Based On Colony Counts For Three Sample Test Volumes

| Sample Size | Bacterial Counts (CFU) | | |
|---|---|---|---|
| | Infection | Possible Infection | No Infection |
| Per 1 ml of urine | 100,000 | 1,000 | 100 |
| Per 10 μl of urine | 1,000 | 10 | 1 |
| Per 1 μl of urine | 100 | 1 | — |

A critical consideration in the cultural diagnosis of UTI's is the choice of media. In order to permit growth of the largest number of species, cultural quantitation methods must be conducted on non-selective, non-inhibitory media (e.g., 5% sheep blood agar, brain heart infusion agar, etc.). Regardless of their purpose as non-selective, selective or differential, most culture media are designed in a manner such that following inoculation of the specimen, the medium is incubated at 35°–37° C., for 18–24 hours or longer, depending upon the organism and medium. Some organisms require different temperatures and/or time of incubation for optimal growth, characteristics which may be helpful in differential diagnosis. Notwithstanding the growth characteristics of the involved microorganism, the treating physician desires as rapid an identification as possible. Thus, primary isolation culture media which permit rapid growth and preliminary presumptive diagnosis of etiological organisms are very desirable. This is of particular importance where immediate treatment is essential.

II. Non-Culture Methods for UTI Diagnosis

Because of the time and manipulation necessary for traditional culture methods, as well as the large number of "negative" specimens, manufacturers and researchers have been very interested in development of rapid urine screening methods. The purposes of these screening methods are: 1) to provide accurate information to the physician in a timely manner, which should correlate with prompt patient care; and 2) to provide rapid elimination of negative specimens, thereby allowing the microbiologist to devote more time to positive specimens, leading to improved cost-effectiveness and efficiency.

Rapid methods described in the literature include microscopic examination (e.g., Gram and acridine orange stains), enzymatic assays (e.g., catalase, glucose oxidase, nitrate reductase, and leukocyte esterase), various endotoxin assays, filtration (e.g., colorimetric), bioluminescent and automated (e.g., photometric detection of growth) procedures. As reviewed by Pezzlo (Pezzlo, "Detection of Urinary Tract Infections by Rapid Methods," Clin. Microbiol. Rev., 1:268, (1988)), these methods have been extensively evaluated. Most compare favorably when a culture method with $\geq 10^5$ CFU/ml is used as a reference. However, these methods compare less favorably with lower colony counts (Pezzlo, at p. 271). A significant disadvantage of these methods is that they only provide a semi-quantitative estimate of the patient's bacteriuria; they do not provide an indication of the genus or species of the organisms(s) present. This is an important consideration, as the physician needs to know the etiologic organisms in order to provide the patient with the optimum antimicrobial treatment.

From the above, it is obvious that although there are many test systems available, they each have characteristics which preclude their use in certain situations. Many of these tests require expensive reagents, technical time, and laboratory equipment. What is needed is a cost-effective method, at least as sensitive and specific as traditional quantitative culture methods. The method should be rapid, reliable, and should provide at least a presumptive diagnosis to the treating physician in as short a time period as possible.

SUMMARY OF THE INVENTION

The present invention describes test media and methods for the growth, isolation, and presumptive identification of bacterial organisms. The present invention contemplates compounds and formulations, as well as methods particularly suited for the detection and presumptive identification of organisms most often associated with urinary tract infections (UTI's).

In one embodiment, the present invention provides a method for detecting the presence of bacterial organisms in a test sample suspected of containing bacteria comprising the steps of: a) inoculating a test medium with a test sample, wherein the medium comprises: i) a chromogenic β-glucuronidase substrate capable of forming a first color upon reacting with β-glucuronidase; ii) a chromogenic arylsulfatase substrate capable of forming a second color upon reacting with arylsulfatase, wherein these first and second colors are visibly distinguishable; and iii) a nutrient base; b) incubating the test medium to produce bacterial colonies of organisms to generate one or more of first and second colors; and c) examining said the medium for i) the presence of bacterial colonies having the first color, ii) the presence of bacterial colonies having the second color; and iii) the presence of bacterial colonies without either the first or second colors. It is not intended that the present invention be limited to a particular variety of colors.

It is also contemplated that the method of the present invention further comprises the step of enumerating said bacterial colonies present on said test medium.

In a preferred embodiment, the test medium of this method further comprises at least one opaque compound. It is particularly preferred that this opaque compound render the test medium white. In one embodiment, the opaque compound is proteinaceous. In a particularly useful embodiment, the proteinaceous compound is a milk-derived preparation. However, in an alternative embodiment, the opaque compound is non-proteinaceous. In one embodiment, the non-proteinaceous opaque compound is selected from the group comprising silicates, oxides, and carbonates. It is not intended that the present invention be limited by the type of opaque compound.

In one embodiment, the test medium of this method further composes at least one amine. It is contemplated that the amine selected from the group consisting of glutamine, glutamic acid, tryptophan, phenylalanine and tyramine can be used with success. It is also contemplated that an amine is selected from the group consisting of octopamine, dopamine and norepinephrine will be used.

In a particularly preferred embodiment, the method further comprises the step of assaying the bacterial organisms in the colonies for the ability to oxidize at least one aromatic amine in the presence of at least one coordinating compound selected from the group comprising manganese, iron, and copper ions. In one embodiment, the aromatic amine is selected from the group comprising tryptophan and tyramine.

In another preferred embodiment, the method further comprises the step of assaying for the presence of pyocyanin in the test medium surrounding the bacterial colonies. In a particularly preferred embodiment, the assaying for the presence of pyocyanin comprises the steps of: i) applying acid to the test medium surrounding the bacterial colonies; and ii) observing for the production of a color change in the test medium. It is particularly contemplated that hydrochloric acid will be used in this assaying. A 2 Normal solution of hydrochloric acid has been found to be particularly useful in this embodiment.

In a preferred embodiment, the method of further comprises the step of assaying the bacterial organisms for the ability to hydrolyze urea. In an additional preferred embodiment, the method further comprises the step of assaying the bacterial organisms for the ability to reduce tellurite.

An alternative embodiment of the present invention comprises a method for detecting the presence of bacterial organisms in a test sample suspected of containing bacteria comprising the steps of: a) inoculating a test medium comprising: i) at least one chromogenic substrate capable of forming colored bacterial colonies upon reacting with an enzyme; ii) at least one proteinaceous opaque compound; and iii) a nutrient base; b) incubating the test medium to produce colored bacterial colonies of organisms; and c) examining the test medium for i) the presence of colored bacterial colonies; ii) the presence of bacterial colonies without color; and iii) the presence of a zone of clearing surrounding said bacterial colonies.

In one embodiment, the proteinaceous opaque compound is a milk-derived preparation. It is particularly contemplated that skim milk or reduced-fat milk will be used as the proteinaceous opaque compound. It is further contemplated that the proteinaceous opaque compound can be irradiation sterilized.

In one embodiment of the method, the substrate is a chromogenic arylsulfatase substrate. In an additional embodiment, the substrate is a chromogenic β-glucuronidase substrate. In yet another embodiment, the substrates comprise a chromogenic arylsulfatase substrate and a chromogenic β-glucuronidase substrate.

An alternative embodiment of the present invention comprises a method for detecting the presence of bacterial organisms in a test sample suspected of containing bacteria comprising the steps of: a) inoculating a solid test medium with test sample, wherein the test medium comprises: i) a chromogenic β-glucuronidase substrate capable of forming a first color upon reacting with β-glucuronidase; ii) a chromogenic arylsulfatase substrate capable of forming a second color upon reacting with arylsulfatase; iii) a proteinaceous, opaque reagent; and iv) at least one compound capable of forming a third color upon reacting with at least one bacterial enzyme, wherein the first, second and third colors are visually distinguishable; b) incubating the test medium to produce bacterial colonies of organisms to generate one or more of these first, second and third colors; c) examining said test medium for i) the presence of bacterial colonies having a first color, ii) the presence of bacterial colonies having a second color; iii) the presence of bacterial colonies having a third color; iv) the presence of bacterial colonies without the first, second or third colors; and v) examining the test medium for the presence of a zone of clearing surrounding the bacterial colonies.

In one embodiment, the bacterial enzyme is selected from the group comprising tryptophan oxidase, phenylalanine deaminase, and tyramine oxidase. In a particularly preferred embodiment, the medium further comprises at least one coordinating compound selected from the group consisting of manganese, copper and iron ions. It is contemplated that these bacterial enzymes and coordinating compounds can be used successfully in any combination of one or more enzymes along with one or more coordinating compound.

In one embodiment, the method further comprises the step of assaying the bacterial organisms for the ability to hydrolyze urea. It is contemplated that this assaying for the ability of the bacterial organisms to hydrolyze urea comprises the steps of i) placing bacterial organisms in a solution comprising urea and a pH indicator; and ii) examining for the production of color. In a particularly useful embodiment, the concentration of urea in the solution is approximately five percent, the concentration of pH indicator is approximately 0.05 percent, and the pH of the solution is adjusted to approximately pH 4 to 7. It is contemplated that a variety of pH indicators will be used. In a particular embodiment, the pH indicator is selected from the group comprising m-cresol purple, phenol red, thymol blue, bromthymol blue, bromcresol purple, xylenol blue, and cresol red. It is not intended that the present invention be limited by the mechanism of the urease test. It is also not intended that the present invention be limited to a particular pH indicator or color.

In another preferred embodiment, the method further comprises the step of assaying bacterial organisms for the ability to reduce tellurite. In a particularly useful embodiment, the assaying for the ability of bacterial organisms to reduce tellurite comprises the steps of i) placing drops of a tellurite salt solution on colonies suspected of being *Enterococcus faecalis;* ii) incubating the bacterial organisms; and iii) examining for the production of a black color. In one embodiment, the tellurite salt solution comprises approximately one percent potassium tellurite. It is not intended that the present invention be limited by the mechanism of the tellurite test. It is also not intended that the present invention be limited to a particular tellurite-containing salt nor produce a particular color upon testing. For example, it is contemplated that use of varying concentrations of tellurite solution may result in the production of a gray color.

In a preferred embodiment of the method, *Escherichia coli,* colonies growing on the test medium are visible to the eye as being red in color, with a halo of clearing in the medium surrounding the colonies. It is also contemplated that *Klebsiella pneumoniae* growing on the medium of the present invention are visible to the eye as being indigo in color and mucoid, with a halo of clearing in the medium surrounding the colonies.

It is further contemplated that *Salmonella choleraesuis* growing on the medium of the present invention are visible to the eye as being brown in color, with brown pigment diffusing from the colonies into the medium. It is also contemplated that *Proteus mirabilis* growing on the medium of the present invention are visible to the eye as being orange in color, with spreading edges and orange pigment diffusing from the colonies into the medium. It is also contemplated that *Klebsiella oxytoca* growing on the medium of the present invention will be visible to the eye as being yellow in color, with yellow pigment diffusing from the colonies and a halo of clearing in the medium surrounding the colonies. It is also contemplated that *Pseudomonas aeruginosa* growing on the medium of the present invention will be visible to the eye as being green in color, with green pigment diffusing from the colonies and a halo of clearing in the medium surrounding the colonies.

In addition, it is contemplated that *Staphylococcus aureus* growing on the medium of the present invention are visible to the eye as being yellow in color, with a halo of clearing in the medium surrounding the colonies. It is further contemplated that *Enterococcus faecalis* growing on the medium of the present invention will be visible to the eye as small and white in color, with a halo of clearing in the medium surrounding the colonies.

In one alternative embodiment, a medium for the identification of bacterial colonies comprising: i) at least one proteinaceous opaque compound; ii) one or more chromogenic substrates; and iii) a nutrient base, is contemplated. In one embodiment, the nutrient base comprises one or more compounds selected from the group comprising soy peptone, meat extract, magnesium sulfate and sodium sulfate. It is further contemplated that other compounds can be used successfully in the nutrient base, including, but not limited to, such compounds as beef extract and chlorides. In one particularly preferred embodiment, the proteinaceous compound is a milk-derived preparation. It is contemplated that a variety of milk-derived compounds can be used with success in the medium of the present invention, including, but not limited to, skim or reduced-fat milk and casein.

One embodiment of the medium includes one or more chromogenic substrates is selected from the group consisting of arylsulfatase substrates, glucuronidase substrates, tryptophan oxidase substrates, and tyramine oxidase substrates.

Another alternative embodiment of the present invention comprises a medium for the identification of bacterial colonies comprising, in mounts sufficient for the growth and differentiation of bacterial colonies: i) at least one chromogenic glucuronidase substrate, ii) at least one chromogenic arylsulfatase substrate; and iii) at least one opaque compound which renders the test medium white. In a particularly preferred embodiment, the opaque compound is non-proteinaceous. It is contemplated that various non-proteinaceous compounds can be used with success in the medium of the present invention including but not limited to, such compounds as silicates (e.g., kaolin and calcinated diatomaceous earth), carbonates (e.g., calcium carbonate), and oxides (e.g., titanium oxide). However, it is also contemplated that various proteinaceous opaque compounds can be used with success, including but not limited to, various milk-derived preparations, such as casein and skim or reduced-fat milk.

It is also contemplated that in one embodiment of the medium, the chromogenic substrate is selected from the group comprising chromogenic arylsulfatase substrates, chromogenic glucuronidase substrates, chromogenic tryptophan oxidase substrates, and chromogenic tyramine oxidase substrates. It is contemplated that these substrates can be successfully used in any combination. For example, the arylsulfatase substrate may be used in combination with either the glucuronidase, tryptophan or tyramine oxidase substrates; the glucuronidase substrate may be used in combination with either the tryptophan or tyramine substrate; and the tryptophan substrate may be used in combination with the tyramine substrate. It is also contemplated that in addition to two substrates used in combination, three or more substrates may be used in combination. In a particularly preferred embodiment, the medium further comprises at least one coordinating compound selected from the group consisting of manganese, copper and iron.

An additional embodiment of the present invention comprises a medium for the identification of bacterial colonies comprising, in amounts sufficient for the growth and differentiation of bacterial colonies: i) at least one casein-containing compound; ii) a chromogenic glucuronidase substrate; iii) a chromogenic arylsulfatase substrate, iv) at least one coordinating compound selected from the group comprising manganese, copper and iron; and v) a gelling agent.

In a preferred embodiment, the chromogenic glucuronidase substrate is selected from the group comprising 6-chloro-3-indolyl-β-D-glucuronide and 5-bromo-6-chloro-3-indolyl-β-D-glucuronide. In an additional embodiment, the chromogenic arylsulfatase substrate is indoxyl-3-sulfate. It is also contemplated that the medium of the present invention further comprising at least one amine selected from the group consisting of glutamine, glutamic acid, tryptophan, phenylalanine, tyramine, octopamine, dopamine and norepinephrine can be used successfully.

GENERAL DESCRIPTION OF THE INVENTION

The present invention is predicated in part on the discovery that various organisms may be differentiated based on differential biochemical reactions observed in an agar medium. The multiple test medium of the present invention permits presumptive and rapid microbiological screening of urine samples and other specimens, without requiring inoculation of multiple agar media, saving time and money. The medium of the present invention permits the inoculation of one plate with subsequent presumptive identification of the most frequently encountered pathogens. This is in contrast to current methods requiring the inoculation of several media commonly used for urine analysis and selective isolation of various organisms (see e.g., Baron and Finegold, at 83) such as blood agar (e.g., trypticase soy agar with 5% sheep blood), Columbia colistin-nalidixic acid agar, (CNA), phenylethyl alcohol agar (PEA), eosin methylene blue agar (EMB), MacConkey and, and/or cystine-lactose-electrolyte deficient (CLED) agar. These non-selective, selective and/or differential media permit the growth of some organisms, but each medium has significant drawbacks.

Non-selective primary growth media such as blood agar permit growth of most urinary tract pathogens. However, pathogens are not significantly differentiated from non-pathogens on these media. Furthermore Proteus, if present swarms rapidly across the entire agar surface, making it impossible to pick isolated colonies. In addition, important spot tests such as the urease spot test cannot be performed directly on cells taken from these and many other media.

Selective and differential media (e.g., MacConkey and EMB [eosin methylene blue]) typically show only one important trait such as lactose fermentation. Although they permit growth and differentiation of a few important pathogens, other pathogens are inhibited. Thus, enumeration of pathogens and normal flora is often impossible on these media. This is highly significant, given the common use of quantitative methods to differentiate between contaminated samples and those representing true UTI's. In view of the serious nature of many UTI's, this is an important consideration.

In addition, these media often interfere with additional reactions important in biochemical differentiation of organisms and confirmation of their identification. For example, while MacConkey agar permits visualization of lactose fermentation, it inhibits the indole spot test, an important test in the differentiation of many organisms, particularly *E. coli*. Furthermore, because it contains compounds inhibitory to gram-positive organisms (e.g., bile salts and crystal violet), these organisms grow poorly or not at all on this medium. Thus, MacConkey and EMB are less than optimal for primary isolation and presumptive identification of many organisms commonly associated with UTI's.

Likewise, CLED has significant disadvantages. Because this medium contains pH sensitive dyes which gradually change in hue as the pH rises or falls, the differential colony coloration on this medium is not as distinct as with MacConkey (which contains precipitating components) and the coloration can be obscured when colonies are overly crowded. Colonial growth after overnight incubation is not as rapid as with other media, but if the medium is incubated longer than 24 hours, lactose fermenters on the plate can turn the entire plate pink, obscuring the presence of non-fermenters. Furthermore staphylococci and enterococci look similar and Shigella species are inhibited due to the absence of electrolytes in this medium.

Moreover, the present invention is designed to overcome some of the problems and limitations of more modern multi-test media for bacterial identification. For example, Fluorocult ECD Medium (E. Merck AG, Darmstadt, Germany) is typical of several new culture media that utilize methylumbelliferyl glucuronide (MUG), a fluorogenic substrate for the β-glucuronidase enzyme. This medium can be used in combination with the indole spot test for reasonably accurate presumptive identification of *E. coli* (Heizmann et al., "Rapid Identification of *Escherichia coli* by fluorocult media and positive indole reaction," J. Clin. Microbiol., 26:2682–2684 [1988]).

A newer modification of MUG-containing culture medium was recently introduced for UTI's and has been described by Orenga et al. ("Urinary Tract Infections: Improved CPS ID, a New Ready-to-Use Medium for Enumeration and Identification of *Escherichia coli*, Proteeae and Enterococcus," Rapid Methods & Automation in Microbiology, London, September 1993). "CPS ID" is a fluorogenic agar medium developed by bioMerieux (La Balme-les-Grottes, France) based on four metabolic tests to identify *E. coli,* Proteeae, and Enterococcus sp. Identification of *E. coli* is based on β-glucuronidase activity and indole positivity. Proteeae are identified based on tryptophan deaminase activity and the indole test. Enterococcus sp. are identified based on β-glucosidase activity.

While these MUG-containing media may provide a presumptive diagnosis, they also have several substantial limitations. The fluorogenic 4-methylumbelliferyl-β-D-glucuronic acid incorporated into the agar for *E. coli* identification must be observed under ultraviolet light and it diffuses substantially when hydrolysed by β-glucuronidase. Thus, it is difficult to use this medium to identify *E. coli* present in a mixed culture. In CPS ID medium, the tryptophan deaminase test is not incorporated into the agar medium but instead is performed as a spot test on suspected colonies. This is relatively inconvenient and increases the likelihood that Proteus colonies will not be recognized. Furthermore the chromogenic β-glucosidase test used in CPS ID medium to recognize Enterococcus is not very specific to this genus as many genera, including most Enterobacteriaceae species are positive for β-glucosidase. CPS ID medium also fails to identify other important urinary tract pathogens such as *K. pneumoniae* and *P. aeruginosa.*

A still newer, modified version of this medium designated "Chromogenic CPS ID" or "CPS2" uses a chromogenic substrate for β-glucuronidase detection. Otherwise this medium is based on the same four metabolic tests as "CPS ID" and has the same limitations as its predecessor (Orenga et al., supra; Orenga et at., "Urinary Tract Infections: Improved CPS ID, a New Ready-m-Use Medium for Enumeration and Identification of *Escherichia coli,* Proteeae and Enterococcus," Abstr. P 14/2, p. 107, Abstracts of the Seventh International 1 Congress on Rapid Methods and Automation in Microbiology and Immunology, London (12–15 Sep., 1993); and Freydiere and Gille, "A New CPS Medium for Rapid Identification and Enumeration of Bacteria in Urine Sample, Abstract P14/5, p. 107, Abstracts, Seventh International Congress on Rapid Methods and Automation in Microbiology and Immunology, London (12–15 Sept., 1993)).

Petri plates which contain several partially-useful culture media have been utilized as an alternative to the shortcomings exhibited by single culture media. For example, Remel Inc. (Lenexa, Kans.) manufactures two products for presumptive identification of urinary tract pathogens. Both products utilize four different media which are pre-dispensed into petri plates which are divided into four compartments (or quadrants; these plates are often referred to as "quad plates"). As described in the "Technical Information" (Remel, Inc., Lenexa, Kans., (1989)), the first quadrant in the "Uropath II Quad" plates contains bile esculin agar, which is useful for differentiation of organisms within the Klebsiella-Enterobacter-Serratia group. The second quadrant contains DNAse Test Agar with toluidine blue, useful for rapid identification of *S. marcescens* and differentiation of Serratia from Enterobacter and Klebsiella. The third quadrant contains phenylalanine to differentiate the Proteeae (based on the phenylalanine deamination reaction demonstrated by Proteus, Providencia and Morganella), and tryptone to detect indole production for coliform identification. The fourth quadrant contains adonitol which serves as a carbon source for fermentation by some genera.

Importantly, the "Uropath II Quad" plates must be inoculated with pure cultures. The medium is therefore not useful for primary isolation from urine specimens. This requires that the culture be first inoculated and incubated on a primary isolation medium for 18–24 hours. Isolated colonies are then picked to the "Uropath II Quad" plate and incubated for 18–24 hours on this medium. Therefore, a minimum of two days is required in order to obtain even a presumptive identification of members within the Enterobacteriaceae. In addition, the media in Uropath II are not useful for *P. aeruginosa* nor the gram-positive bacteria.

A second, similar product is "Urinary Quad," described in the "Technical Information" (Remel, Inc., Lenexa, Kans., (1989)). The first quadrant in the "Urinary Quad" plate contains dextrose agar, which is used to obtain a total count of organisms in the specimen. A catalase test may be performed on growth on the first quadrant. The second quadrant contains Simmon's citrate agar, for differentiation of Enterobacteriaceae and Pseudomonas based on citrate utilization. The third quadrant contains Levine's EMB agar, which is useful for differentiation of Enterobacteriaceae based on lactose fermentation. The fourth quadrant contains urea agar and gelatin. The urea agar differentiates enteric bacilli based on urease activity. The gelatin is included in order to permit testing for gelatin liquefaction useful in the differentiation of Pseudomonas.

Although the "Urinary Quad" plates are intended for use as primary isolation media, like the "Uropath II Quad" plates, they have significant disadvantages. First, with the exception of the dextrose agar, the other media in the plate are useful only for differentiation of gram-negative bacilli. There is no use for the agars in quadrants two through four for the identification of gram-positive organisms such as *S. aureus, S. saprophyticus,* and Enterococcus. A catalase test may be done with bacteria grown on the dextrose agar which might give a clue as to the presence of gram-positive organisms, especially if there is little or no growth in the other quadrants. However, this imparts only limited information and additional tests will be needed for identification of the organisms. Furthermore, if there is a mixed culture of gram-negative and gram-positive organisms, it is likely that the gram-positives will be missed.

Quad plates have other disadvantages in that they are relatively expensive, as well as being more difficult and tedious to inoculate, given the limited space available to distribute the inoculum. Furthermore, the technician must perform four streaking operations on each plate. In addition to the quad-plates, other plate configurations are commercially available, such as tri-plates with three compartments, and bi-plates with two compartments. The standard size for all of these plates is 100×15 mm (See e.g., Fisher Scientific Catalog, 1993/94, at pp. 634–636). The surface area available in each compartment is inversely proportional to the number of compartments. Thus, while these plates require less manipulation than the quad plates, there are fewer media included, limiting the utility of the plates.

As discussed above, the problems associated with commonly used media highlight the need for a more suitable medium. For example, the ideal medium should support rapid growth of gram-positive as well as gram-negative organisms, permitting detection of either major group. In addition, the medium should permit differentiation of all organisms most commonly associated with UTI's, without the need for supplementation with other media in compartmented petri plates. The medium described in this invention accomplishes these objectives.

The present invention provides media formulations which are useful for the differential analysis of all bacterial species most commonly associated with UTI's. These same microorganisms are also among the principal pathogens found in septicemia and bacteremia.

The medium is designed to take full advantage of unique biochemical reactions which occur within or due to the metabolism of these important bacterial species. When grown on the preferred embodiment of the present invention, E. coli colonies are large and red, usually with a faint halo of clearing at the colonial periphery. K. pneumoniae colonies are large and mucoid with a blue/black or blue/gray color and a faint halo of clearing at the colonial periphery. K. oxytoca colonies are large, produce a bright yellow pigment, coloring the colony and the surrounding medium, and usually have a faint halo of clearing around the colonies. P. mirabilis colonies are large, slightly spreading and are colored orange along with the surrounding medium. P. aeruginosa colonies are large, colored turquoise green to yellow green due to the pyocyanin pigment that they produce, and are surrounded by a halo of clearing of proteolysis in the surrounding medium. S. choleraesuis colonies are large and brown in color, with diffusion of brown pigment into the medium, but with no halo of clearing. E. faecalis grows as bright white pinpoint colonies, which precipitate casein under the colonies and proteolyze casein around the colonies. S. aureus colonies are medium sized and golden yellow in color, also with a clear halo of proteolysis.

The medium also takes into consideration the biochemical properties of human urine, the biological fluid from which these bacteria are often isolated. For example, the red color of E. coli colonies observable after as few as three hours of incubation, is due to the presence of the β-glucuronidase enzyme. This is related to human physiology, as the human liver has enzymes which conjugate glucuronic acid onto aromatic compounds to make them water-soluble and readily excreted by the kidneys into the urine. Most E. coli strains possess a characteristic β-glucuronidase which removes the glucuronic acid from these conjugates in order to permit utilization of the glucuronic acid as a carbon source, thereby permitting the growth of organisms in the urinary tract. The organism may also use the enzyme to decrease the concentration of potentially toxic glucuronide-conjugated aromatics in the urine.

Lactose fermentation is also used to help differentiate E. coli, as lactose positive strains will exhibit a partial clearing or halo around the colonies due to the action of a β-galactosidase (along with other enzymes involved in lactose catabolism). This clearing is not due to proteolysis, but instead appears to be the result of casein solubilization by organic acids produced by fermentation of lactose in the skim milk constituents of the medium. Solubilization can be confirmed by placing a drop or two of 2N HCl onto the clear zone surrounding a colony. Upon exposure to the acid, the zone will turn cloudy due to reprecipitation of the casein. If acid is placed in the clear zone around organisms which truly proteolyze the casein, as opposed to solubilizing it, the zone remains clear.

Differentiation of E. coli from similar-looking colonies such as the less commonly isolated glucuronidase positive strains of Salmonella and Shigella spp., as well as red-pigmented strains of Serratia is possible based on the absence of zones of clearing around these organisms, due to their lack of the β-galactosidase enzyme. In addition, an indole spot test is readily performed, which provides additional confirmation of colonies as E. coli (indole positive). E. coli is the only species reported to be positive for β-glucuronidase, β-galactosidase and indole.

Identification of K. pneumoniae is also related to normal human metabolism, as the human liver also has enzymes which conjugate sulfate onto unwanted aromatic compounds. K. pneumoniae characteristically has an arylsulfatase enzyme which functions to remove the sulfate from these conjugates in order to use the sulfate as a sulfur source. In a manner similar to that of E. coli, this organism may also use the enzyme to decrease the concentration of potentially toxic sulfate-conjugated aromatics in the urine. Thus, K. pneumoniae also has the biochemical capabilities necessary for colonization of the urinary tract. On the medium of the present invention, lactose fermenting (i.e., lactose positive) K. pneumoniae strains will also exhibit the halo of partial clearing described for E. coli.

Differentiation of K. pneumoniae from similar-looking arylsulfatase positive species such as the less commonly isolated Klebsiella and Enterobacter spp., (e.g., K. planticola, E. aerogenes and E. gergoviae; Yamada et al., "Comparative immunological studies on arylsulfatase in bacteria of the family Enterobacteriaceae: Occurrence of latent arylsulfatase protein regulated by sulfur compounds and tyramine," J. Bacteriol., 133:536–541 [1978]) is aided by indole and urease spot tests which may be conducted using growth from the medium of the present invention. K. pneumoniae isolates are typically indole negative and weakly urease positive.

An additional Klebsiella species, K. oxytoca also produces a distinct coloration on the medium of the present invention. This organism is negative for arylsulfatase but instead produces large, bright yellow colored colonies during overnight incubation. Although other bacteria may grow as large yellow colonies on the medium of the present invention (e.g., Pantoeae sp.), no other organism produces this distinctive diffusible pigment excreted from the cells. In addition, indole and urease spot tests can be performed to confirm the identification of K. oxytoca, colonies of which are typically positive in the indole test and weakly positive in the urease test.

Identification of P. mirabilis is based on its strong tryptophan oxidase (also known as tryptophan deaminase and probably the same enzyme as phenylalanine deaminase) activity. This enzyme, produced by most members of the Proteeae, catalyzes the deamination of tryptophan into indole pyruvic acid. This deaminase activity is directly detectable in the medium of the present invention by the production of orange colonies due to the complexation of the indole compound by manganese or copper. This orange color may be observed after as little as four hours of incubation, thereby providing a relatively rapid presumptive identification of P. mirabilis.

P. mirabilis swarms very little on the medium of the present invention, in itself a significant advantage over other commonly used media. Nevertheless, it is still possible to observe jagged, spreading edges on colonies of P. mirabilis which is a distinctly characteristic trait helpful in recognition of this organism. As with E. coli and Klebsiella, the urease and indole spot test reactions are useful in providing additional confirmation of colonial identity and of course the biochemical relevance of the urease test to bacteria isolated from urine is obvious. P. mirabilis is negative in the indole test and strongly positive in the urease test.

Identification of S. choleraesuis is based on the oxidation of tyramine to hydroxyphenylacetaldehyde by the enzyme tyramine oxidase, which results in the production of a brown pigment by colonies when manganese or copper are present in the medium formulation. S. choleraesuis colonies are brown in color, with defined margins. This is in clear contrast to Proteus colonies, which are orange in color, and spread with uneven edges.

Differentiation of *S. choleraesuis* from similar looking tyramine oxidase-positive colonies such as *P. pseudoalcaligenes* is easily determined, based on the reactions observed in an oxidase spot test. *S. choleraesuis* is oxidase negative, whereas *P. pseudoalcaligenes* is oxidase positive.

Identification of *P. aeruginosa* is based on the production and secretion of pyocyanin, a turquoise green, soluble pigment produced by most *P. aeruginosa* strains. *P. aeruginosa* also exhibits a strong proteolytic activity which clears the casein in the agar underneath the colony and forms a halo of clearing around the colony. While others have investigated the use of milk medium for detection of *P. aeruginosa* (see e.g., Brown and Foster, "A simple diagnostic milk medium for *Pseudomonas aeruginosa*, J. Clin. Pathol., 23:172–177 [1970]), the medium of the present invention provides a much more rapid color production and hydrolysis reaction. As indicated in Brown and Foster (p. 174), "[o]ne disadvantage of the simple milk agar is that it takes 48 hours for full pigmentation and hydrolysis to show." Indeed, they found that the best pigment production was obtained by 24 hours of incubation at 37° C., followed by 24 hours at 20° C. They eventually added 25% nutrient broth to their medium in order to permit observation of pigmentation and hydrolysis after 24 hours of incubation. This is in contrast to the method and medium of the present invention, which facilitates observable and rapid pigment production and casein hydrolysis at one incubation temperature within as little as seven hours. In addition, to further confirm the identification of suspected *P. aeruginosa* colonies, the color of the colonies will change from green to pink within a few seconds upon exposure to a drop or two of 2N HCl. An oxidase spot test can also be used to confirm that the organism is not a member of the Enterobacteriaceae.

*E. faecalis* is differentiated from the gram-negative organisms by its bright white, very small, almost pinpoint colonies on the medium. This organism also produces a halo of clearing around the colony due to proteolysis of the casein in the agar. Furthermore, in areas of heavy colonial growth, production of acid by lactose fermentation on this medium precipitates the milk casein and causes a characteristic hazy cloudiness.

To confirm the presence of suspected *E. faecalis*, a drop or two of 1% potassium tellurite may be dispensed onto the colonies. If a colony is capable of reducing tellurite, it will turn black within one hour. *E. faecalis* is the only member of the Enterococcus genus which is capable of reducing tellurite (R. R. Facklam and J. A. Washington, III, "Streptococcus and related catalase-negative gram-positive cocci," in A. Balows et al. (eds.), *Manual of Clinical Microbiology*, American Society for Microbiology, pp. 238–257 [1991]). An additional "PYR" test (pyrrolidonyl arylamidase) used in microbiology labs can also be performed on these colonies. This test is helpful in differentiating enterococci from streptococci. The enterococci are positive whereas all streptococci except *S. pyogenes* are negative (Facklam and Washington, at p.252).

Unlike *E. faecalis*, *S. aureus* produces medium-sized, opaque, golden yellow colonies on the medium. As are many of the above organisms, *S. aureus* is usually proteolytic, producing a clear halo in the agar. To confirm the presence of suspected *S. aureus* colonies, the coagulase test may be performed. It is contemplated that any means to test for the activity of coagulase can be used in conjunction with the medium of the present invention, including slide and tube coagulase tests. Typically, *S. aureus* is positive, whereas the great majority of other organisms are coagulase negative.

*S. saprophyticus* produces medium-sized, opaque white colonies on the medium, permitting its differentiation from *E. faecalis* and *S. aureus*. This organism is strongly proteolytic and produces a clear halo in the medium surrounding the colonies.

TABLE 5

Colony Characteristics Of Important Organisms On The Medium Of The Present Invention

| Organism | Colony |
| --- | --- |
| E. coli | Large, red colony, with surrounding zone of clearing |
| K. pneumoniae | Large, blue-gray mucoid colony, with surrounding zone of clearing |
| K. oxytoca | Large, yellow colony, with yellow pigment diffusing from the colony and usually with a surrounding zone of clearing |
| S. choleraesuis | Large, brown colony, with brown color in medium surrounding colony; with no zone of clearing |
| P. mirabilis | Large, orange, uneven, slightly spreading colony, with orange color in medium surrounding colony; with no zone of clearing |
| P. aeruginosa | Large, green colony, with surrounding zone of clearing and turquoise green or yellow-green pigment diffusing from colony |
| E. faecalis | Small, white colony, with casein precipitation and surrounding zone of clearing |
| S. aureus | Medium, yellow colony, usually with surrounding zone of clearing |
| S. saprophyticus | Medium, white colony, with surrounding zone of clearing |

The composition of the present multiple test medium is optimized to permit the most ready differentiation of these organisms. The following table summarizes the colony characteristics for the organisms most commonly isolated from UTI's, when grown on a preferred embodiment of the medium of the present invention.

As shown in the above table, the organisms most commonly associated with urinary tract and other infections may be readily distinguished based on their colony characteristics, when grown on the medium of the present invention. The following table presents a summary of colony characteristics as well as supplementary spot tests which can be used to help confirm the identity of these important species after their cultivation on the medium of the present invention. In this Table, the dagger (†) is used to indicate spot tests which are conducted either on colonies present on the medium or with colonies picked from the medium. The coagulase test is therefore included in this designation.

Other organisms, including additional members of the Enterobacteriaceae, as well as various non-glucose fermenters, and gram-positives have also been grown on the medium of the present invention. For example, *Streptococcus agalactiae* (group B strep) grows as small, white colonies, with a halo of clearing due to proteolysis. *Aerococcus urinae* grows as pinpoint red colonies (i.e., β-glucuronidase positive) with no clearing. *Salmonella arizonae* (Salmonella subspecies 3) grows as large, red (i.e., β-glucuronidase positive) colonies with no clearing. *Corynebacterium renale* grows as small orange colonies with weak zones of clearing due to proteolysis. Importantly, the results of this survey indicate that these other species do not give color reactions which closely resemble those of the species shown in Table 6, and would not be mistaken as such.

Nonetheless, it is clearly contemplated and exemplified above that the medium of the present invention will be also useful for the growth and presumptive identification of organisms other than those listed in the above tables.

TABLE 6

Colonial Morphology And Spot Test Reactions*

| Test | Pos. Rxn. | E.c. | P.m. | K.p. | K.o. | S.c. | P.a. | E.f. | S.s. | S.a. |
|---|---|---|---|---|---|---|---|---|---|---|
| β-glucuronidase | Red | + | − | − | − | − | − | − | − | − |
| β-galactosidase | Clearing | + | − | + | + | − | − | − | − | − |
| Indole † | Blue | + | − | − | + | − | − | − | − | − |
| Trptophan oxidase | Orange | − | + | − | − | − | − | − | − | − |
| Urease † | Red | − | + | +/− | +/− | − | − | − | − | − |
| Arylsulfatase | Blue/Black | − | − | + | − | − | − | − | − | − |
| Tyramine oxidase | Brown | − | − | − | − | + | − | − | − | − |
| Pyocyanin | Turquoise | − | − | − | − | − | + | − | − | − |
| Pyocyanin acid reaction † | Pink | − | − | − | − | − | + | − | − | − |
| Oxidase † | Purple | − | − | − | − | − | + | − | − | − |
| Proteolysis | Clearing | − | − | − | − | − | + | + | + | + |
| Coagulase † | Coagulation | − | − | − | − | − | − | − | − | + |
| Tellurite reduction | Black | − | − | − | − | − | − | + | − | − |
| Excreted Pigment | Yellow | − | − | − | + | − | − | − | − | − |
| Cellular Pigment | Yellow | − | − | − | − | − | − | − | − | + |

*The abbreviations used in the above Table are as follows:
Pos. Rxn = Positive reaction
E.c. = E. coli
P.m. = P. mirabilis
K.p. = K. pneumoniae
K.o. = K. oxytoca
S.c. = S. choleraesuis
P.a. = P. aeruginosa
E.f. = E. faecalis
S.s. = S. saprophyticus
S.a. = S. aureus
+ = Positive test result
− = Negative test result It is also contemplated that, in addition to the spot tests described above, other tests will be used in conjunction with the medium of the present invention. For example, unlike many other differential media, one of the major advantages of the medium of the present invention is that important reactions such as indole, urease, catalase, and tellurite reduction are not interfered with by the constituents in the medium or the metabolic end products produced by cultures growing on the medium.

DETAILED DESCRIPTION OF THE INVENTION

The present invention contemplates an indicator plate that is generally useful in the identification of bacteria. This medium and method are particularly targeted toward three of the most important species associated with UTI's. As indicated in the Experimental section below, initial investigations were directed toward the development of a single solid plated medium containing chromogenic chemistries to test three biochemical reactions useful in identifying the organisms most commonly associated with UTI's. The initial focus was directed to the simultaneous testing for a combination of three important enzymes produced by three important bacteria: glucuronidase (for E. coli), arylsulfatase (for K. pneumoniae), and urease (for P. mirabilis).

As microbiologists and media developers have long recognized, it is very difficult to successfully combine multiple test reactions in one medium. This is especially true for media in which pH changes are significant due to their detrimental effects on other reactions. Such difficulties were encountered in the development of the present invention, during which approximately a thousand reagents and reagent combinations were tested.

Inclusion of the pH-based urease test reagents in the medium interfered with the testing of other enzyme systems. For example, when phenol red, the pH indicator used in most urease testing methods was included in the medium, the presence of urease positive organisms caused a color change throughout most of the medium, obscuring or altering the other color changes observable on the medium of the present invention. This is of special concern with urease positive organisms which tend to swarm, such as P. mirabilis. It was observed that growth of P. mirabilis on medium formulations containing pH indicators could change the color of the entire plate of medium. Conversely, in formulations of the medium containing lactose, the presence of lactose-utilizing bacteria such as E. coli, K. pneumoniae and E. faecalis tends to lower the pH and interfere with the urease reactions.

In order to avoid these problems, yet provide a reliable test to aid in the differentiation of the Proteeae, a tryptophan oxidase test was invented and substituted for the urease test for identification of P. mirabilis. In many aspects, this tryptophan oxidase test is preferable to the urease test. As discussed further below, the urease test is not specific for the detection of urea hydrolysis, as it really tests for an increase in pH. In contrast, the tryptophan oxidase test is more specific, as it tests for the presence of an enzyme which oxidizes tryptophan to indole pyruvic acid, and does not depend upon a pH change for its detection.

As an alternative to incorporating the urease test into the agar medium, a confirmatory urease spot test was also developed as part of this overall invention to be used in conjunction with the tryptophan oxidase test, as the preferred testing method with suspected colonies of Proteus. Unlike many other culture media (e.g., blood agar), the medium of the present invention does not interfere with the urease spot test (i.e., cause a false positive reaction).

The present invention was developed in a complex, multi-variant, step-wise fashion, with each medium component tested in varying concentrations and the reactions of various organisms observed. First, the use of Sal-glc for the glucuronidase test and Ind-SO$_4$ for the arylsulfatase test were optimized in order to color glucuronidase positive colonies (e.g., *E. coli*) red, and arylsulfatase positive colonies (e.g., *K. pneumoniae*) indigo. During the process of optimizing the concentration of substrates for these enzymes, it was also noted that inclusion of tyramine was important in obtaining good induction of the arylsulfatase enzyme.

Next, various milk products were tested for their ability to provide an opaque white background for optimal detection and sensitivity of the red and blue chromogenic tests. In addition, it was fortuitously observed that *P. aeruginosa* colonies produce a strong green color on this medium, enabling detection and differentiation of this organism.

Furthermore, milk provides a high contrast opaque white background for performing a tellurite spot test directly on the growth present on an inoculated plate, a test which is very useful in the identification of *E. faecalis*. In this test, a drop of tellurite solution is added to a colony and the reaction observed. A colony capable of reducing the tellurite will become black in color within approximately one hour.

Inclusion of milk also provides the basis for two additional important and useful tests in the medium of the present invention. First, it provides a non-chromogenic means of testing for the presence of the important enzyme β-galactosidase. Colonies of *E. coli* and *K. pneumoniae* grow with surrounding areas of clearing (i.e., halos or zones) in the medium due to utilization of lactose in the milk. For these organisms, the halo is the result of solubilization, rather than degradation of the casein proteins in milk. By using milk in this novel way, β-galactosidase can be tested simultaneously with both β-glucuronidase (important for *E. coli*) and arylsulfatase (important for *K. pneumoniae*). Milk clearing also provides advantages over some β-galactosidase testing media such as CLED with Andrade's indicator, on which incubation over a certain proscribed time may result in the masking of the lactose fermentation reaction. On the present medium, the halo is not adversely affected by increasing the incubation time.

Second, inclusion of milk provides a ready means to test for proteolysis. Proteolysis is a characteristic property of many important pathogenic bacteria such as *P. aeruginosa*, *E. faecalis*, *S. aureus*, and *S. saprophyticus*. Unlike *E. coli* and *K. pneumoniae* which solubilize the milk proteins, these organisms actually degrade the milk proteins by proteolysis so that a permanent clear halo of proteolysis is formed. Importantly, the gram-positive organisms grow well on the medium of the present invention, in contrast to other media commonly used with urine specimens which contain inhibitory compounds (e.g., the crystal violet and bile included in MacConkey).

It was next observed that inclusion of tryptophan in the medium to induce the *E. coli* tryptophanase enzyme is beneficial in enhancing the indole spot test. This test may be conducted on colonies growing on the medium of the present invention by either placing a small drop of indole test reagent directly on a test colony, or by removing a small portion of the test colony to a filter paper impregnated or saturated with an indole test reagent. Unlike many commonly used chromogenic culture media (e.g., MacConkey), the indole test reaction is not inhibited by growing organisms on the media of the present invention.

Next, the formulation was optimized to inhibit swarming of Proteus on the medium. If swarming organisms are present on an agar plate, it is difficult or impossible to pick a single colony for pure culture. By inhibiting the swarming phenomenon, the medium of the present invention allows the technologist to successfully isolate a pure culture for any necessary further studies. By inhibiting swarming, this medium also facilitates identification of other microorganisms which may be present in the sample being analyzed. This is a very important feature of the medium of the present invention, as many commonly used selective and non-selective media do not adequately inhibit swarming.

In one set of experiments using various salts, it was determined that sulfate salts were preferable to chloride salts to minimize swarming. Also during the course of these investigations, it was determined that the inclusion of manganese inhibits the swarming of *P. mirabilis*.

In subsequent experiments use of manganese in the medium led to several very important discoveries. First, it was observed that in the presence of this metal, colonies of *S. choleraesuis* are brown in color. This color production was determined to be due to their ability to oxidize tyramine in the medium and to form hydroxyphenylacetaldehyde and subsequent oxidation or complexation of this aldehyde compound by manganese ions to produce a brown pigment. Second, it was also discovered that *P. mirabilis* colonies were orange on this medium due to their ability to oxidize tryptophan in the medium to form indole pyruvate, followed by subsequent complexation of this compound by manganese ions to form an orange pigment. Inclusion of metals such as manganese and copper were found to be very useful in catalyzing these chromogenic reactions.

Next, several agents were tested for their ability to enhance pyocyanin production by *P. aeruginosa*. First, in the work done with tyramine, the unexpected observation was made that tyramine stimulated the synthesis of pyocyanin. Second, magnesium has been reported to stimulate pyocyanin synthesis (see e.g., E. O. King et al., "Two Simple Media for the Demonstration of Pyocyanin and Fluorescein," J. Lab. & Clin. Med., 44:301–307, 1954; and J. F. MacFaddin, *Media for Isolation-Cultivation-Identification-Maintenance of Medical Bacteria*, Williams & Wilkins, [1985], p. 652–656). This observation was confirmed, and magnesium was found to be beneficial and without any deleterious effects in the medium of the present invention. Third, in work with *P. aeruginosa*, the unexpected observation was made that glutamate and glutamine stimulated synthesis of pyocyanin. These compounds were tested along with several other amino acids and it was confirmed that they were beneficial and without deleterious effects. In the course of these experiments, the unexpected observation was made that phenylalanine was also beneficial and without deleterious effects. In contrast, several other amino acids did not help increase the production of pyocyanin. However, in later experiments, the surprising observation was made that the presence of glutamate and glutamine extends the shelf life of the spot indole test.

Once these reactions were characterized, the effects of various nutrient peptones and extracts on the chromogenic reactions were studied. Based on numerous tests using various types of peptones and peptone preparations, soy peptone was determined to provide the best results. Additional studies on peptone optimization to maximize the spot indole reaction and growth of Staphylococcus sp., were then performed. In these experiments, it was found that brain heart infusion (BHI) and meat extract provided the best results. It was also observed that *S. aureus* colonies are a distinctive yellow color and are proteolytic on this medium, whereas *S. saprophyticus* colonies are white and proteolytic on the medium. These observations are very significant, as many of the selective and differential media used for UTI's, most notably EMB and MacConkey are inhibitory for gram-positive organisms such as Staphylococcus and Enterococcus. Thus, the present invention provides a differential medium which supports good growth of both gram-negative and gram-positive organisms. As two of the most common UTI etiologic agents are *E. coli* (gram-negative) and *S. saprophyticus* (gram-positive), the medium of the present invention provides the advantage that both organisms grow well and are distinguishable.

After the medium components were optimized for the reactions observable on the plate, spot tests used to confirm the identification of various species were studied and optimized. For example, spot indole, urease and tellurite reduction, tests were fine-timed so as to avoid interference among the multiple test systems while providing strong, easy to interpret reactions.

Importantly, not only is the medium of the present invention suitable for the presumptive identification of the organisms most commonly associated with UTI's, the method and medium may also be utilized in conjunction with traditional diagnosis of UTI's. For example, unlike media which are selective for particular organisms (e.g., MacConkey, which permits growth of gram-negatives, but inhibits gram-positive organisms) and media which are dispensed in quad plates, the medium of the present invention may be used to determine colony counts from urine samples. In addition to standard streak plate methods, the medium and method of the present invention may be used with pour plate techniques. Thus, the medium is highly versatile and solves many of the problems associated with other media for microbiological analysis.

Definitions

The terms "sample" and "specimen" in the present specification and claims are used in their broadest sense. On the one hand they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, as well as solid tissue. These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

Whether biological or environmental, a sample suspected of containing microorganisms may or may not first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention to, following subjecting a sample to a conventional enrichment means, subjecting the resultant preparation to further purification such that pure or substantially pure cultures of a strain of a species of interest are produced. This pure culture may then be analyzed by the medium and method of the present invention.

As used herein, the term "organism" is used to refer to any species or type of microorganism, including but not limited to bacteria, yeasts and other fungi, and protozoans.

As used herein, the term "culture" refers to any sample or specimen which is suspected of containing one or more microorganisms. "Pure cultures" are cultures in which the organisms present are only of one genus and species. "Mixed cultures" are cultures in which more than one genus and/or species of microorganism are present.

As used herein, the terms "microbiological media" and "culture media," and "media" refer to any substrate for the growth and reproduction of microorganisms. "Media" may be used in reference to solid plated media which support the growth of microorganisms. Also included within this definition are semi-solid and liquid microbial growth systems including those incorporate living host organisms, as well as any type of media.

As used herein, the common meaning of the term "peptones" is contemplated, namely a chemically indefinite term used to describe a water-soluble product obtained after hydrolysis of proteins (e.g., digestion of red meat, vegetative material or casein). The present invention contemplates the use of plant, milk (casein), and/or meat peptones. These peptones may be produced by acids or enzymes. Protein hydrolysis results in a mixture of free and polymerized amino acids (i.e., peptides) including proteoses; all may remain in solution after heating to 100° C. (J. F. MacFaddin, at p. 1). Peptones are also important for the nucleic acid fractions, minerals and vitamins they provide growing cultures.

As used herein, the term "agar" is used in a broad, generic sense, and refers to the various grades of agar extracted from natural sources such as kelp, as well as compounds produced synthetically. Thus, encompassed within this term are all gelling compounds or agents used in microbiological media, such as alginates, gelatins, gellans, etc., regardless of their source. It is also contemplated that agar(s) and other gelling agents used in the present invention may be obtained commercially from any supply company, such as Difco (e.g., Bacto-agar), BBL, Oxoid, Marcor, or any other source.

As used herein, the term "selective media" refers to media which support the growth of particular organisms of interest but inhibit other organisms. Such inhibition may result due to medium constituents such as compounds which are selectively toxic, as well as the end-products of microbial metabolism produced by organisms which utilize the medium constituents.

As used herein, the term. "differential media" refers to media which support the growth of various organisms, but permit visual differentiation between the different genera or species. For example, a carbohydrate and pH indicator may be included in a differential medium. If an organism is capable of fermenting the carbohydrate and lowering the pH in the medium, a color change will occur. If on the other hand an organism is incapable of fermenting the carbohydrate, the pH will not be lowered and the color will not change. It is contemplated that the colony characteristics will permit differentiation as well. For example, one organism may produce a red colored colony on the medium while another species will be observed as a blue or colorless colony. While some media are either selective or differential, some media are both selective and differential. Examples of media with characteristics of both selective and differential media include such media as eosin methylene blue ("EMB") and MacConkey, both of which contain compounds which inhibit gram-positive organisms, while allowing most gram-negative organisms to grow and produce colored colonies due to the utilization of medium constituents.

As used herein, the term "chromogenic" compound refers to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the term "coordinating compound" is used in reference to compounds as well as elements and ions which may be involved in producing chromogenic reactions. This term includes, but is not limited to such metals as manganese, copper, and iron, as well as other elements. It is also contemplated that these coordinating compounds may be complexed with other compounds.

As used herein, the term "amino acid" is used in reference to any of the subunits which contain both the carboxyl (COOH) and amino group ($NH_2$), which may be polymerized to form proteins. It is not intended that this term be limited to only those amino acids which are naturally occurring. Thus, synthetic and modified amino acids are included within this broad definition, as are both the L- and D- forms.

As used herein, the term "amino" (or "amino group") is used in reference to a chemical group (—$NH_2$), which can form —$NH_3^+$, upon addition of a proton. As used herein, the term "amine" is used in its usual chemical definition. In particular, this term is used in reference to any compound which may be derived from ammonia by replacement of one or more of its hydrogen atoms by another group (e.g., a hydrocarbon). Included within this definition are primary, secondary, and tertiary amines, as well as aliphatic, aromatic and mixed aliphatic-aromatic amines. As used herein, the term "aromatic amine" is used in reference to amines which include an aromatic structure, such as a benzene ring.

As used herein, the term "opaque" is used in reference to compounds and reagents which produce an opaque medium. The term is used to refer to formulations which prevent the transmission of light through the medium. This is in contrast to formulations which permit the transmission of light (e.g., trypticase soy agar, nutrient agar, etc.). It is contemplated that various opacity-producing compounds will be useful in the present invention, particularly as compounds that produce a light (e.g., white) medium including, but not limited to milk, kaolin, calcinated diatomaceous earth and other silicates, calcium carbonate and other carbonates, and titanium oxide (e.g., titanium dioxide) and other oxides. In some embodiments, casein-containing compounds are used as opacity-producing compounds. Thus, it is contemplated that proteinaceous, as well as non-proteinaceous compounds will be utilized in the medium of the present invention.

As used herein, the term "proteinaceous" refers to any compound containing proteins, while the term "non-proteinaceous" refers to any compound which does not include a protein component.

As used herein, the term "skim milk" refers to milk with a reduced fat content. This term encompasses milks commercially available as "lowfat" or "nonfat." This term encompasses, but is not limited to bovine milk.

As used herein, the term "milk-derived preparation," refers to any composition which contains substances derived from milk. It is contemplated that this definition encompass proteins and other substances (e.g., lactose) present in milk.

As used herein, the terms "zone of clearing," "halo" and "halo of clearing" refer to the area of clearing around the colonies of some organisms grown on the medium of the present invention. This clearing may result from the utilization or the solubilization of constituents of the opaque compound. As the organisms grow on the medium, utilization or solubilization of these constituents causes the opaque quality of the medium around the colonies to become clear (i.e., transparent or translucent). While some organisms grown on this medium produce very distinct zones of clearing which are readily visually apparent, other organisms produce weaker zones, wherein the zones are not as clear or distinct.

As used herein, the term "swarming" is used in reference to the growth of Proteus on media, in particular semi-solid or solid plated agar. Swarming is a phenomenon associated with motile organisms, particularly *P. mirabilis*, in which a group of organisms moves outwards from the colony as a unified mass. Often, the growth on solid media appears as a series of concentric rings surrounding the colony, usually shaped like a target. While Proteus is often associated with swarming growth, it is contemplated that other organisms grown on the medium of the present invention may exhibit swarming. It is also contemplated that the swarming of such organisms may be inhibited by the medium of the present invention.

As used herein, the term "spreading" is used in reference to the colony morphology of some organisms, in Which the colony edges are not smooth or "entire." Rather, when viewed either by eye or through a dissecting microscope, the edges of the colonies are usually irregular. The usual meaning of the word is contemplated, as used by those skilled in the art of observing bacterial colony morphology. For example, it is contemplated that some organisms, including but not limited to *P. mirabilis* will exhibit some degree of spreading colony morphology on the medium of the present invention.

As used herein, the term "mucoid" is used in reference to the colony morphology exhibited by some organisms in which the colony consistency is similar to that of mucus. Again, as with all other terms used by those skilled in the art of observing bacterial colony morphology, the usual meaning of the word is contemplated. For example, it is contemplated that some organisms, including but not limited to *K. pneumoniae* will produce mucoid colonies on the medium of the present invention. However, it is also contemplated that some *K. pneumoniae* colonies will not be mucoid when grown on the medium of the present invention.

As used herein, the term "diffusible pigment" refers to the production and release of pigmented (i.e., colored) substances from bacterial cells and colonies. When grown on microbiological medium, diffusible pigments are often observable, as they may impart a color to the medium. For example, pyocyanin is a diffusible pigment produced by most *P. aeruginosa* strains, which colors the medium surrounding colonies of this organism a green color. This green color may range from a yellow-green to a blue-green or turquoise, depending upon the strain and the medium constituents. There are numerous diffusible pigments produced by various organisms. It is not intended that the present invention will be limited to pyocyanin or any other specific diffusible pigment.

As used herein, the term "primary isolation" refers to the process of culturing organisms directly from the sample. Thus, primary isolation involves such processes as inoculating an agar plate from a culture swab, urine sample, etc. Primary isolation may also be done in liquid or semi-solid media.

As used herein, the term "presumptive diagnosis" refers to a preliminary diagnosis which gives some guidance to the treating physician as to the etiologic organism involved in the patient's disease. Presumptive diagnoses are often based on "presumptive identifications," which as used herein refer to the preliminary identification of a microorganism based on observation such as colony characteristics, growth on primary isolation media, gram stain results, etc.

As used herein, the term "definitive diagnosis" is used to refer to a final diagnosis in which the etiologic agent of the patient's disease has been identified.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); tool (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); MRAD (megarad); °C. (degrees Centigrade); CFU (colony forming units); ELISA (Enzyme-Linked Immunosorbent Assay); TSA (trypticase soy agar); EMB (eosin methylene blue medium); MacConkey (MacConkey medium); CLED (cystine lactose electrolyte deficient agar); salmon-glc, or Sal-glc (salmon-beta-D-glcA; 6-chloro-3-indolyl-β-D-glucuronic acid, monocyclohexylammonium salt, Biosynth); Magenta-glc or mag-glc (Magenta-β-D-glcA; 5-bromo-6-chloro-3-indolyl-β-D-glucuronic acid cyclohexylammonium salt, Biosynth); Ind-glc (Indoxyl-glucuronide, Biosynth); Ind-SO$_4$ (3-indoxyl sulfate; Sigma); Mag-SO$_4$ (magenta sulfate; 5-bromo-6 -chloro-3-indolyl sulfate; Biosynth); X-SO$_4$ (5-bromo-4-chloro-3-indolyl sulfate; Biosynth); YEP (yeast enriched peptone, Deltown); proteose peptone #3 (Proteose Peptone #3, Difco Laboratories); PP (proteose peptone, Marcor); UHT (ultra high temperature pasteurization; used in reference to commercially prepared milk such as the UHT milk distributed by Real-Fresh of Visalia, Calif.); skim milk powder (Oxoid milk powder, Oxoid); Redigel (RCR Scientific, Goshen, Ind.); Oxoid (Oxoid, Basingstoke, England); BBL (Becton Dickinson Microbiology Systems, Cockeysville, Md.); DIFCO (Difco Laboratories, Detroit, Mich.); Marcor (Marcor Development, Hackensack, N.J.); Sheffield (Sheffield Products, Norwich, N.Y.); Champlain (Champlain Industries, Clifton, N.J.); Intergen (Intergen, Inc., Purchase, N.Y.); U.S. Biochemical (U.S. Biochemical Corp., Cleveland, Ohio); Scientific Products (McGraw Park, Ill.); Sigma (Sigma Chemical Co., St. Louis, Mo.); Biosynth (Biosynth AG, Skokie, Ill.); and Deltown (Deltown Chemurgic, Greenwich, Conn.).

In the experimental section that follows, unless otherwise specified, the L- form of all amino acids was used. In general, the various media were prepared by autoclaving an 8% solution of skim milk powder separately from the remainder of the ingredients. After autoclaving for 5 minutes at 121° C., the skim milk solution was added to the other ingredients and the agar medium was poured into petri plates. Agar plates were inoculated by streaking and incubated overnight at 30°–35° C. in an ambient gas atmosphere. The following Table lists the principal bacterial strains used in the following Examples. Additional species and strains representing the Enterobacteriaceae, various gram-positive and numerous other organisms not shown in this Table were also tested.

TABLE 7

Principal Bacteria Strains Tested

| Organism | Source and Number | Type Strain? |
|---|---|---|
| E. coli | ATCC 11775 | Yes |
| E. faecalis | ATCC 19433 | Yes |
| K. pneumoniae | ATCC 13883 | Yes |
| K. oxytoca | BIOLOG 1046 | No |
| P. mirabilis | ATCC 7002 | No |
| P. aeruginosa | ATCC 10145 | Yes |
| S. aureus | ATCC 12600 | Yes |
| S. choleraesuis | ATCC 13312 | Yes |
| S. agalactiae | ATCC 13813 | Yes |
| S. saprophyticus | ATCC 15305 | Yes |

The examples below are grouped in the order shown in the following table.

TABLE 8

EXAMPLES

| GROUP | SUBJECT | EXAMPLE NUMBERS |
|---|---|---|
| I | Glucuronidase and Arylsulfatase Test Reactions | 1–5 |
| II | Milk Formulations and Clearing Reactions | 6–7 |
| III | Effect of Tryptophan on the Indole Spot Test | 8 |
| IV | Inhibition of Swarming by Proteus and Other Advantages of Manganese Ions | 9–12 |
| V | Effects of Added Amino Acids and Magnesium Ions | 13–16 |
| VI | Comparison of Various Salts | 17–18 |
| VII | Effect of Peptones on Chromogenic Reactions and Organism Growth | 19–22 |
| VIII | Optimization of Peptones, Extracts, and Amino Acids for Growth of Staphylococcus, and Stabilization of the Indole Spot Test | 23–28 |
| IX | Development of Various Spot Tests | 29 |

Group I

Glucuronidase & Arylsulfatase Test Reactions

In this group of experiments, the use of various substrates for the chromogenic glucuronidase and arylsulfatase reactions were tested.

EXAMPLE 1

Determination of Minimum Satisfactory Chromogenic Substrate Concentrations

Most chromogenic substrates are very expensive, and yet it is important to use a concentration that is sufficient to provide adequate coloration of bacterial colonies. In this experiment, the minimum satisfactory chromogenic substrate concentrations for glucuronidase and arylsulfatase reactions were determined.

1. Ind-$SO_4$ and Sal-Glc

A base medium was selected initially which contained a low level of salt to minimize swarming by Proteus. This base medium contained agar (15 g/l), YEP (4 g/l), $KH_2PO_4$ (0.1 g/l), $K_2HPO_4$ (0.1 g/l), and $MgSO_4$ (0.1 g/l). This base medium was used to determine minimum satisfactory concentrations of Ind-$SO_4$ and Sal-glc. Ind-$SO_4$ and Sal-glc concentrations of 25 mg/l, 50 mg/l, 75 mg/l, and 100 mg/l were tested, as were 50 mg/l X-$SO_4$, and 50 mg/l X-glc. The media were prepared with the various additives added to the base medium described above, inoculated with an arylsulfatase positive strain (*K. pneumoniae*) and a glucuronidase positive strain (*E. coli*) and observed.

*K. pneumoniae* was used to test the arylsulfatase chemistry. It was observed that even the highest concentration of chromogenic arylsulfatase substrate (100 mg/l) did not work (i.e. the colonies were white instead of blue-gray). However, tyramine and other amines act as inducers of the arylsulfatase enzyme (T. Harada and Y. Murooka, "Participation of tyramine oxidase in multiple control of bacterial arylsulfatase synthesis," Mem. Inst. Sci. Ind. Res., Osaka Univ., 37:45–58 [1980]). Therefore tyramine crystals were added to the surface of the plate, and within about an hour, the *K. pneumoniae* colonies turned a dark blue-black color.

*E. coli* was used to test the glucuronidase chemistry. It was observed that colonies were white at 25 mg/l Sal-glc, pink at 50 mg/l, red at 75 mg/l and 100 mg/l, and white on 50 mg/l X-glc.

Based on these results, 75 mg/l was found to be a satisfactory concentration of Sal-glc and 100 mg/l was found to be a satisfactory concentration of Ind-$SO_4$, so long as tyramine is also present at adequate levels.

2. Effects of Inducers of Arylsulfatase and Glucuronidase

Additional variations were tested in this group of experiments. Here, the base medium consisted of agar (15 g/l), YEP (4 g/l), $Na_2HPO_4$ (3.5 g/l), $KH_2PO_4$ (1.5 g/l), and $MgSO_4$ (0.1 g/l). The base medium was prepared as above, with aliquots divided into groups designated "A" and "B," which contained various additional compounds.

In group A, there were two batches, each of which contained Sal-glc (50 mg/l). The first contained no additional additives and the other contained β-methyl glucuronic acid (100 mg/l), an inducer of the *E. coli* glucuronidase enzyme. On both batches, *E. coli* colonies were pink, so the less expensive β-methyl glucuronic acid did not enhance the colony coloration.

In group B, there were three batches, each comprised of base medium and 100 mg/l Ind-$SO_4$. The first batch contained no additional additives. The second batches contained potential inducers of the arylsulfatase enzyme, specifically 500 mg/l tyramine HCl, and 500 mg/l chondroitin-$SO_4$ (Sigma). *K. pneumoniae* colonies were white on all three formulae after overnight incubation at 35° C.

After several days of additional incubation at room temperature on the tyramine plate, *K. pneumoniae* and *S. choleraesuis* turned blue-black. From this experiment, it appeared that the arylsulfatase activity was stronger after the culture was shifted to room temperature. Another surprising observation was made that *P. aeruginosa* colonies were green on the tyramine-containing plate.

EXAMPLE 2

Determination of Satisfactory Tyramine Concentration

As noted above in the previous example, tyramine had a clear beneficial effect on the arylsulfatase reaction. Thus, this next experiment was designed to determine a satisfactory tyramine concentration for production of the strongest arylsulfatase reaction.

In this example, the base medium consisted of agar (15 g/l), YEP (2 g/l), Ind-$SO_4$ (100 mg/l), $MgCl_2$ (0.1 g/l), and $FeCl_2$ (0.1 g/l). This base medium was divided into 10 batches. Batch 1, with no additions, served as a control. Batch 2 contained 50 mg/l tyramine HCl; batch 3 contained 100 mg/l; batch 4 contained 200 mg/l; batch 5 contained 500 mg/l; batch 6 contained 1000 mg/ml; and batch 7 contained 2000 mg/ml. Batches 8, 9 and 10 also contained 2000 mg/l tyramine, but there was a further addition of Ind-$SO_4$ (100 mg/l) in batch 8, chondroitin sulfate (100 mg/ml) in batch 9, and taurine (100 mg/l) in batch 10. After these media were mixed and autoclaved, plates were poured and inoculated with organisms. The following tables show the results for each batch and four organisms after incubations for different time periods and temperatures.

TABLE 9

Results After 24 Hours Incubation at 35° C.

| Batch | K. pneumoniae | P. aeruginosa | P. mirabilis | S. choleraesuis |
|---|---|---|---|---|
| 1 | White | White | White | White |
| 2 | Light Gray | White | White | White |
| 3 | Light Gray | White | White | White |
| 4 | Light Gray | White | White | White |
| 5 | Darkest | Light Green | White | White |
| 6 | Medium Gray | Green | White | White |
| 7 | Light Gray | Green | White | Light Blue |
| 8 | Light Gray | Green | White | Light Blue |
| 9 | Medium Gray | Green | White | White |
| 10 | Light Gray | Green | White | White |

TABLE 10

Results After 2 Additional Days Of Room Temperature Incubation

| Batch | K. pneumoniae | P. aeruginosa | P. mirabilis | S. choleraesuis |
|---|---|---|---|---|
| 1 | White | White | White | White |
| 2 | Light gray | White | White | White |
| 3 | Light gray | White | White | White |
| 4 | Light gray | White | White | Light Gray |
| 5 | Dark | White | White | Light Gray |
| 6 | Dark | Green | White | Light Gray |
| 7 | Medium Gray | Green | White | Light Gray |
| 8 | Darkest of All | Green | White | Darkest of All |
| 9 | Medium Gray | Green | White | Light Gray |
| 10 | Dark | Green | White | Light Gray |

Several surprising observations were made. First, it was determined that 200 mg/l Ind-$SO_4$ seemed to give a significantly darker arylsulfatase reaction than 100 mg/l. Second, it was observed that synthesis of the green pyocyanin pigment of *P. aeruginosa* was stimulated by tyramine at levels above 500 mg/l. Third, it was observed that the arylsulfatase of *K. pneumoniae* is induced more strongly and easily than the arylsulfatase of *S. choleraesuis* and that by keeping the tyramine level relatively lower, these species could be distinguished.

EXAMPLE 3

Evaluation of Ind-SO$_4$ and X-SO$_4$

This experiment was designed as a continuation of the previous two examples, in that in this experiment the effects of various concentrations of Ind-SO$_4$ and X-SO$_4$ were evaluated. The base medium consisted of agar (15 g/l), skim milk powder (16 g/l), proteose peptone #3 (3 g/l), monosodium glutamate (2 g/l), NaCl (5 g/l), and tyramine HCl (500 mg/l). The base medium was prepared and then divided into batches. Following sterilization, the media were dispensed, inoculated with various organisms, incubated at 30° C., and observed. The following table shows the compounds added for each batch, as well as pertinent information regarding the observed colony characteristics of the organisms.

These results indicated that batches 4, 5, 9, 11, and 12 produced the darkest reactions overall. Ind-SO$_4$ and X-SO$_4$ appear to be roughly equivalent and there is no advantage to combining them. Based on these results, a good minimum concentration to use was found to be approximately 200 mg/l.

TABLE 11

| Batch | Compound Added | Observations |
| --- | --- | --- |
| 1 | 70 mg/l Ind-SO$_4$ | *K. pneumoniae* is blue-black |
| 2 | 100 mg/l Ind-SO$_4$ | *K. pneumoniae* is darker blue-black than Batch 1 |
| 3 | 150 mg/l Ind-SO$_4$ | *K. pneumoniae* is darker blue-black than Batch 2 |
| 4 | 200 mg/l Ind-SO$_4$ | *K. pneumoniae* is darker blue-black than Batch 3 |
| 5 | 250 mg/l Ind-SO$_4$ | About the same as Batch 4 |
| 6 | 70 mg/l X—SO$_4$ | *K. pneumoniae* is pastel blue |
| 7 | 100 mg/l X—SO$_4$ | *K. pneumoniae* darker pastel blue than Batch 6 |
| 8 | 150 mg/l X—SO$_4$ | *K. pneumoniae* darker pastel blue than Batch 7 |
| 9 | 200 mg/l X—SO$_4$ | *K. pneumoniae* darker pastel blue than Batch 8 |
| 10 | 35 mg/l Ind-SO$_4$ + 35 mg/l X—SO$_4$ | *K. pneumoniae* blue-black (like Ind-SO$_4$) |
| 11 | 75 mg/l Ind-SO$_4$ + 75 mg/l X—SO$_4$ | *K. pneumoniae* blue-black (like Ind-SO$_4$), darker than Batch 10 |
| 12 | 100 mg/l Ind-SO$_4$ + 100 mg/l X—SO$_4$ | *K. pneumoniae* blue-black (like Ind-SO$_4$), about the same as Batch 11 |

EXAMPLE 4

Evaluation of Ind-SO$_4$ and Mag-SO$_4$

In this experiment, the effectiveness of various concentrations of Magenta-SO$_4$ ("Mag-SO$_4$") and Ind-SO$_4$ were compared. Several compounds other than peptones were also tested in order to produce a darker arylsulfatase reaction. In this experiment, the base medium consisted of agar (17 g/l), skim milk powder (16 g/l), soy peptone (6 g/l), monosodium glutamate (2 g/l), glutamine (1 g/l), tryptophan (500 mg/l), phenylalanine (250 mg/l), tyramine (250 mg/l), red-glc (70 mg/l), MnCl$_2$ (50 mg/l), and CuSO$_4$ (50 mg/l).

Seven batches of base medium were prepared and the reagents listed in the following table were added. Following inoculation and incubation, the arylsulfatase reactions were observed.

TABLE 12

| Batch | Reagents |
| --- | --- |
| 1 | 100 mg/l Ascorbic Acid and 100 mg/l Mag-SO$_4$ |
| 2 | 100 mg/l Mag-SO$_4$ |
| 3 | 200 mg/l Mag-SO$_4$ |

TABLE 12-continued

| Batch | Reagents |
| --- | --- |
| 4 | 100 mg/l Mag-SO$_4$ and 100 mg/l Ind-SO$_4$ |
| 5 | 200 Mg/l Mag-SO$_4$ and 200 mg/l Ind-SO$_4$ |
| 6 | 250 mg/l Ind-SO$_4$ |
| 7 | 250 mg/l Ind-SO$_4$ and 1 g/l MgCl$_2$ |

Batch 5 produced the darkest overall reaction for *K. pneumoniae*, but the presence of Mag-SO$_4$ at 200 mg/l gave Salmonella colonies a pink color (i.e., a weak positive reaction). The same problem was observed with batch 3. Therefore, these combinations were found to be less desirable.

Batch 6 (with 250 mg/l Ind-SO$_4$) worked well, but Batch 7 (with an additional 1 g/l MgCl$_2$) provided the best overall results. Due to the presence of MgCl$_2$ in this batch, green pyocyanin production by *P. aeruginosa* was stimulated, enhancing the differentiation capabilities of the medium.

EXAMPLE 5

Sal-Glc Concentrations

In this example, various concentrations of Sal-glc were tested. The base recipe consisted of agar (17 g/l), skim milk powder (16 g/l), Marcor soy peptone (6 g/l), Na$_2$SO$_4$ anhydrous (2.5 g/l), MgSO$_4$ anhydrous (0.6 g/l), monosodium glutamate (2 g/l), glutamine (1 g/l), tryptophan (500 mg/l), phenylalanine (250 mg/l), tyramine free base (200 mg/l), Ind-SO$_4$ (250 mg/l), and MnSO$_4$ (50 mg/l). The medium was divided into 5 batches and varying concentrations of Sal-glc, tested with and without other compounds.

The following table shows the components of each batch and the reactions observed following inoculation and incubation of the media with various organisms. Of these formulations, batch 5 produces the most acceptable results with the minimal amount of Sal-glc. While higher concentrations of Sal-glc provide more intense colors, the expense of this compound makes higher concentrations uneconomical in most situations.

TABLE 13

| Batch | Sal-Glc | Observations |
| --- | --- | --- |
| 1 | 30 mg/l | *E. coli* is white/pink |
| 2 | 40 mg/l | *E. coli* is pink |
| 3 | 50 mg/l | *E. coli* is dark pink |
| 4 | 60 mg/l | *E. coli* is light red |
| 5 | 70 mg/l | *E. coli* is red |

Group II

Milk Formulations and Clearing Reactions

In the following experiments, different milk preparations were tested for their ability to provide an opaque, white background for optimal detection and sensitivity of the chromogenic tests. The addition of milk also provides an easy means to test for proteolytic and lactose utilization. Thus, these reactions were also observed.

EXAMPLE 6

Use of Skim Milk to Test for Lactose Utilization and/or Proteolysis

In this experiment, skim milk plates were prepared with varying combinations of different peptones, extracts, and lactose, and were tested for the lactose utilization reactions.

A simple base medium was used, consisting of agar (15 g/l), NaCl (5 g/l), and Oxoid skim milk (16 g/l). Following inoculation, the plates were incubated at 30° C. for approximately 24 hours.

The following table lists the components added to each batch of test medium, as well as the reactions observed for *E. coli, S. choleraesuis, K. pneumoniae* and *P. aeruginosa.* Because *E. coli* and *K. pneumoniae* are both lactose-fermenting organisms, it was expected that they would produce zones of clearing due to casein solubilization. For *P. aeruginosa,* the zone of clearing is due to proteolysis.

TABLE 14

| Batch | Ingredients | E. coli | S. choler. | K. pneumo. | P. aerug. |
|---|---|---|---|---|---|
| 1 | Tryptone (10 g/l) and yeast extract (5 g/l) | +++ | – | No Growth | +++ |
| 2 | Tryptone (10 g/l), yeast extract (5 g/l) and lactose (2 g/l) | +++ | – | ++/+++ | +++ |
| 3 | Tryptone (10 g/l) | +++ | – | + | +++ |
| 4 | Tryptone (10 g/l), and lactose (2 g/l) | +++ | – | + | +++ |
| 5 | Tryptone (5 g/l) | +++ | – | ++ | +++ |
| 6 | Tryptone (5 g/l) and lactose (2 g/l) | +++ | – | ++/+++ | +++ |
| 7 | Proteose peptone #3 (3 g/l) | +++ | – | ++ | +++ |
| 8 | Proteose peptone #3 (3 g/l) and lactose (2 g/l) | +++ | – | ++ | +++ |

S. choler. = S. choleraesuis
K. pneumo. = K. pneumoniae
P. aerug. = P. aeruginosa
+++ = Very good zone of clearing due to casein solubilization or proteolysis
++ = Good zone of clearing
+ = Observable zone of clearing
– = No zone of clearing Based on the above results, it appears that there is no great effect of peptone or supplementation of 0.2% lactose on the casein solubilization reaction. However, yeast extract was found to inhibit pyocyanin production by *P. aeruginosa.* For example, on batches 1, 2 and 4, the *P. aeruginosa* colonies were light green, on batches 3 and 6, the colonies were a medium green color, and on batches 5, 7 and 8, the colonies were dark green. Thus, it appears that overall, batches 5, 6, 7 and 8 contain the best combinations of ingredients.

In the course of this and other, similar experiments, the surprising observation was made that *P. aeruginosa* produced dark green colonies with a pronounced clearing of proteolysis around the colonies. It was very easy to distinguish between protein solubilization due to lactose fermentation and true proteolysis with an easy to perform and rapid spot test. In this spot test, a drop or two of 2N HCl was added to the cleared zone and observed for the production of opacity. If true proteolysis has occurred, the cleared zone remains clear. If solubilization has occurred due to lactose utilization, the cleared zone becomes opaque.

EXAMPLE 7

Milk Formulations

In this Example, different milk preparations were tested to determine the best milk preparations and milk concentration to use for the medium of the present invention. A 0.1% glycerol solution was also tested in conjunction with one batch of skim milk powder.

The base medium consisted of agar (17 g/l), soy peptone (6 g/l) and NaCl (5 g/l). To this base medium varying concentrations of liquid or powdered milk were added and dispensed into petri plates. Following inoculation and incubation of organisms on the plated media, the reactions were observed. The table below lists the milk preparations and concentrations, as well as observations regarding the reactions produced by organisms grown on these different formulations.

TABLE 15

| Batch | Milk Preparation | Clearing Reactions |
|---|---|---|
| 1 | 1.6% Oxoid Skim Milk Powder | Good |
| 2 | 2.0% Oxoid Skim Milk Powder | Better than Batch 1 |
| 3 | 1.6% Oxoid Skim Milk Powder, with 0.1% Glycerol | P. aeruginosa was yellow; more lysis observed |
| 4 | 3 ml/20 ml UHT Milk (lowfat) | No clearing |
| 5 | 4 ml/20 ml UHT Milk (lowfat) | No clearing |
| 6 | 2 ml/20 ml Condensed Milk | Good |
| 7 | 2.5 ml/20 ml Condensed Milk | Better than Batch 6 |
| 8 | 5.0 ml/20 ml Condensed Milk | Not as good as Batch 6 |

The milk powder plates were chalky off-white in color. In comparison, the UHT milk plates were slightly whiter and the condensed milk plates were slightly more yellow. Based on the reactions produced by cultured organisms, the skim milk preparations are superior to the lowfat UHT milk. Also, based on these results, the optimum concentration of skim milk was estimated to be between 1.6 and 2% (batches 1 and 2). However, condensed milk at 100 ml to 125 ml per liter of base medium also provides excellent results (batches 6 and 7).

This example demonstrates some of the major advantages in the use of milk protein as a base in a chromogenic agar medium, including increased color contrast (i.e., providing clearer reactions), lower concentrations of expensive chemicals are needed, and the proteolysis and protein solubilization reactions that are observable. Although such opacity-creating inorganic compounds as kaolin are also contemplated in the present invention, these alternative opacity-producing compounds do not permit the observation of some important phenotypic reactions due to solubilization, degradation, and/or precipitation of caseins. However, it is not intended that the present invention be limited to the use of opacity compounds which permit the observation of these phenotypic reactions.

Group III

Effect of Tryptophan on the Indole Spot Test

The indole spot test is a very important and useful test in continuing the identification of *E. coli* (indole positive) and *P. mirabilis* (indole negative). Since other enteric bacteria can be positive for glucuronidase and lactose utilization, they can be confused with *E. coli.* Therefore, in this experiment, added tryptophan was tested for its effect on the spot indole test. As described below, surprising observations were made. The effect of incubation temperature and an atmosphere with increased $CO_2$ were also tested.

EXAMPLE 8

Effect of Tryptophan, and Temperature and $CO_2$ Incubation Conditions

In this experiment the base medium consisted of agar (15 g/l), skim milk powder (16 g/l), NaCl (10 g/l), proteose peptone #3 (3 g/l), monosodium glutamate (2 g/l), tyramine HCl (500 mg/l), and Ind-$SO_4$ (250 mg/l). The following table shows the additional compounds and/or special incubation conditions and the results for each batch. These media were sterilized, dispensed, inoculated and incubated as described above (unless otherwise indicated incubation was conducted at 30° C. in ambient atmosphere).

TABLE 16

| Batch | Compound Added | Results |
| --- | --- | --- |
| 1 | Control (30° C.) | Spot indole negative |
| 2 | 500 mg/l L-Tryptophan (30° C.) | Spot indole positive; *P. aeruginosa* slightly lighter; |
| 3 | 2000 mg/l L-Tryptophan (30° C.) | Spot indole positive; *P. aeruginosa* much lighter, |
| 4 | 37° C. | *K. pneumoniae* slightly lighter and more mucoid; *P. aeruginosa* slightly darker |
| 5 | 37° C. + $CO_2$ | *P. aeruginosa* much lighter; Clear zones less distinct; *K. pneumoniae* lighter and more mucoid |

As indicated above, addition of 500 mg/l of tryptophan was found to be beneficial in that it resulted in strongly positive spot indole test reactions. However, if the concentration of tryptophan is too high, it has a detrimental effect on the green color of *P. aeruginosa* colonies. Incubation at 37° C. was satisfactory, but incubation with elevated $CO_2$ was detrimental to coloration of *K. pneumoniae* and *P. aeruginosa* colonies, and caused the zones of clearing in the skim milk to be much less distinct.

Group IV

Inhibition of Swarming by Proteus and Other Advantages of Manganese Ions

In this group of experiments the ability of various compounds to inhibit the swarming of Proteus was investigated. The effects of these compounds on the other organisms were also of interest and recorded. For example, of particular interest was the impact of various metal ions on pigment production by *P. aeruginosa*, as well as the chromogenic reactions.

EXAMPLE 9

Effect of Manganese, Menadione, Bismuth, Tellurite, and Miscellaneous Minerals

In this experiment, the effects of manganese, menadione, bismuth, tellurite, and miscellaneous minerals on the reactions of the present base medium were studied. In particular the ability of the compounds/compound combinations to inhibit the swarming of Proteus colonies, while supporting good growth of other organisms was of interest.

The base medium consisted of agar (15 g/l), skim milk powder (16 g/l), proteose peptone #3 (3 g/l), monosodium glutamate (2 g/l), NaCl (5 g/l), tyramine HCl (500 mg/l), and Ind-$SO_4$ (250 mg/l). The base medium was divided into 20 batches and various compounds listed in the following table were added. The media were dispensed and inoculated as described above. Following inoculation, the plates were incubated at 30° C. and observed.

TABLE 17

| Batch | Compounds Added | Observations |
| --- | --- | --- |
| 1 | None (Control) | |
| 2 | 4 g/l Milk powder | Discarded, medium foamed |
| 3 | 4 g/l Na caseinate | Discarded, medium foamed |
| 4 | 4 g/l Casein | Perhaps slightly better for *K. pneumoniae* and *E. faecalis* |
| 5 | 10 mg/l Menadione bisulfite | No difference |
| 6 | 1 mg/l Menadione bisulfite | No difference |
| 7 | 200 mg/l $MnCl_2$ | Inhibits *P. mirabilis* swarming; Salmonella orange/brown; *P. aeruginosa* a little darker |
| 8 | 200 mg/l $MnCl_2$ + 100 mg/l Urea | Inhibits *P. mirabilis* swarming; Salmonella orange/brown; *P. aeruginosa* a little darker |
| 9 | 200 Mg/l $MnCl_2$ + 200 mg/l Urea | Inhibits *P. mirabilis* swarming; Salmonella orange/brown; *P. aeruginosa* a little darker |
| 10 | 200 mg/l $MnCl_2$ + 500 mg/l Urea | Inhibits *P. mirabilis* swarming; Salmonella orange/brown; *P. aeruginosa* a little darker; *K. pneumoniae* darker with orange halo |
| 11 | 200 mg/l $MnCl_2$ + 1000 mg/l Urea | Inhibits *P. mirabilis* swarming; Salmonella orange/brown; *P. aeruginosa* a little darker; *K. pneumoniae* darker with orange halo |
| 12 | 200 mg/l $MnCl_2$ + 200 mg/l Sodium thiosulfate | Inhibits *E. coli* clearing |
| 13 | 200 mg/l Bismuth citrate + 200 mg/l Sodium thiosulfate | *E. coli*, Salmonella, *K. pneumoniae*, *P. mirabilis* all gray black |
| 14 | 5 mg/l Potassium tellurite | *E faecalis* black; *P. aeruginosa* green; enterics inhibited |
| 15 | 10 mg/l Potassium tellurite | *E. faecalis* black; *P. aeruginosa* green; enterics inhibited |
| 16 | 200 mg/l $CaCl_2$ | No difference or slightly worse |
| 17 | 200 mg/l $MgCl_2$ | No difference or slightly worse |
| 18 | 200 mg/l $MgSO_4$ | No difference or slightly worse |
| 19 | 200 mg/l $Na_4PPi$ | No difference or slightly worse |
| 20 | 200 mg/l $KH_2PO_4$ | No difference or slightly worse |

This experiment produced several very surprising and very important results. First, the addition of manganese was found to be very beneficial in that it inhibited Proteus from swarming, even in the presence of urea. Furthermore, it was observed that in the presence of manganese, *S. choleraesuis* produced a brown pigment. It was later determined that this pigment was due to the ability of *S. choleraesuis* to deaminate tyramine to hydroxyphenylacetaldehyde, which is subsequently oxidized and/or complexed by manganese to form a brown pigment. Manganese also produced a slight stimulation of green pyocyanin production by *P. aeruginosa*. Importantly, manganese had no detrimental effects.

In this experiment, it was also observed that *E. faecalis* colonies are dark black in the presence of tellurite. This has also turned out to be a rapid, easy to perform diagnostic test useful in the invention. However, because tellurite is toxic to many bacteria (including most enteric bacteria), it could not be merely added to the medium without detrimental effects. Rather, a tellurite spot test was developed as a substitute. In this test, suspected colonies of *E. faecalis* may be tested by adding a drop or two of potassium tellurite directly onto colonies suspected of being *E. faecalis*. *E. faecalis* colonies reduce the tellurite and mm black after about one hour of room temperature incubation.

EXAMPLE 10

Effects of Manganese Concentration Alone, and in Combination With Other Additives In this experiment, several media were tested, all of which contained manganese. The base medium consisted of agar (15 g/l), skim milk powder (16 g/l), casein (4 g/l), proteose peptone #3 (3 g/l), monosodium glutamate (2 g/l), NaCl (5 g/l), Ind-$SO_4$ (250 mg/l), mag-glc (70 mg/l), tyramine HCl (300 mg/l), and $MnCl_2$ (50 mg/l). The base medium was divided into 8 batches and various compounds listed as shown in the following table were added. Following inoculation, the plates were all incubated at 30° C. and then observed.

TABLE 18

| Batch | Compounds Added | Observations |
|---|---|---|
| 1 | None (Control) | |
| 2 | Tyramine 200 mg/l | Same as 1 |
| 3 | $MnCl_2$ 150 mg/l | Same as 1; Salmonella very slightly darker yellow |
| 4 | Tyramine (200 mg/l) + $MnCl_2$ (150 mg/l) | Same as 1; Salmonella slightly darker |
| 5 | Tryptophan (100 mg/l) | Good spot indole; *P. mirabilis* slightly orange (swarms a little) |
| 6 | Tryptophan (200 mg/l) | Poor spot indole; *P. mirabilis* orange (swarms a little more) |
| 7 | Tryptamine (100 mg/l) | Same as 1; *K. pneumoniae* slightly darker; *P. mirabilis* slightly inhibited |
| 8 | Chondroitin $SO_4$ (100 mg/l) | Same as 1; *K. pneumoniae* slightly darker; *P. mirabilis*, *E. coli* slightly inhibited |

This experiment produced several very surprising and very important results. First, increasing the manganese and/or tyramine concentration had little or no beneficial effect. More importantly, with batches 5 and 6, it was observed that a good spot indole test was obtained with as little as 100 mg/l of added tryptophan. Even more surprising and important was the observation that, with both tryptophan and manganese present in the medium, *P. mirabilis* colonies and the surrounding medium turned bright orange. The color was clearly stronger with 200 mg/l tryptophan compared to 100 mg/l. It was strongly suspected that the orange color was due to deamination of tryptophan to indole pyruvate by *P. mirabilis*, followed by complexation of indole pyruvate by manganese to produce an orange pigment.

EXAMPLE 11

Oxidation or Complexation of Indole Pyruvate Tested With Various Minerals

It was observed in the previous example that *P. mirabilis* produces a strong orange color in the presence of tryptophan and manganese. It was hypothesized that this was due to oxidation or complexation of indole pyruvate by manganese. In this experiment, the ability of various minerals were tested in order to determine which provided the best enhancement of color formation from indole pyruvate. To observe the rate and degree of color formation, one mg/ml indole pyruvate was dissolved in water with NaOH added to neutralize the acid. Based on these results, it was concluded that Mn, Cu, Fe, or combinations of the two were effective in generating colored compounds from indole pyruvate. The following table lists the minerals and the different colors produced.

TABLE 19

| Batch | Mineral | Color of Mineral in Water | Color of IPA and Mineral | Color of IPA Mineral, and HCl |
|---|---|---|---|---|
| 1 | $MnCl_2$ | Light pink/Clear | Yellow-Orange | Pink-Orange |
| 2 | $CoCl_2$ | Blue | Blue | Yellow-Clear |
| 3 | $CuSO_4$ | Blue | Fluorescent Yellow-Green | Yellow-Clear |
| 4 | $ZnSO_4$ | Clear | Clear | Clear |
| 5 | $NiCl_2$ | Turquoise | Turquoise | Clear |
| 6 | $MnCl_2$ and $CuSO_4$ | — | Yellow/Black/Brown | Pink-Orange |
| 7 | $Fe_2(SO_4)_3$ | Light Yellow | Red | Red |

EXAMPLE 12

Comparison of Manganese and Copper, Alone and in Combination

In this experiment, manganese and copper were tested for their effects on the chromogenic reactions observed in this medium. The base medium consisted of agar (17 g/l), skim milk powder (16 g/l), soy peptone (6 g/l), monosodium glutamate (2 g/l), glutamine (1 g/l), tryptophan (500 mg/l), phenylalanine (250 mg/l), tyramine HCl (250 mg/l), Ind-$SO_4$ (250 mg/l), and Sal-glc (70 mg/l). The medium was divided into four batches and varying concentrations of minerals were added as shown in the following table. The medium was inoculated and reactions observed at 24 hours.

TABLE 20

| Batch | Compounds Added | Color of *P. mirabilis* |
|---|---|---|
| 1 | Control | Light orange |
| 2 | Control with 50 mg/l $MnCl_2$ | Dark orange |
| 3 | $CuSO_4$ (50 mg/l) | Red-orange |
| 4 | $MnCl_2$ (50 mg/l) and $CuSO_4$ (50 mg/l) | Darker orange than Batch 2 |

Both manganese and copper gave good coloration of *P. mirabilis* and did not have substantial adverse effects. It was then decided to use manganese alone because the orange color produced was distinctly different from the red color produced by *E. coli* from Sal-glc and the brown color produced by *S. choleraesuis* from tyramine.

Group V

Effects of Added Amino Acids and Magnesium Ions

In this set of experiments, various amino acids were tested for their ability to enhance pyocyanin production by *P. aeruginosa*, as well as the other chromogenic reactions. In addition, the impact of $Mg^{++}$ on pyocyanin production was studied.

EXAMPLE 13

Effect of Glutamic Acid, Yeast Extract, and Incubation Temperature and Atmosphere In this experiment, the effects of glutamic acid, yeast extract, and incubation temperature and atmosphere conditions were tested.. The base medium consisted of agar (15 g/l), Oxoid milk powder (16 g/l), NaCl (10 g/l), tyramine HCl (500 mg/l), and Ind-$SO_4$ (250 mg/l). The base medium was divided into 10 batches, each batch receiving additional compounds as shown in the following table. Following inoculation of each batch with *E. coli*, *Salmonella*, *K. pneumoniae*, and *P. aeruginosa*, the plates were incubated at 30° C., 26° C., or 35° C., as shown in the following table.

TABLE 21

| Batch | Added Compound | Incubation Temperature |
|---|---|---|
| 1 | Proteose Peptone #3 (3 g/l), plus monosodium glutamic acid (2 g/l) | 30° C. |
| 2 | Proteose Peptone #3 (3 g/l), plus yeast extract (1 g/l) and monosodium glutamic acid (2 g/l) | 30° C. |
| 3 | Proteose, Peptone #3 (10 g/l) | 30° C. |
| 4 | Proteose Peptone #3 (10 g/l), plus yeast extract (1 g/l) | 30° C. |
| 5 | Tryptone (10 g/l) | 30° C. |
| 6 | Tryptone (10 g/l), plus yeast extract (1 g/l) | 30° C. |
| 7 | Tryptone (10 g/l), plus yeast extract (1 g/l) and monosodium glutamic acid (2 g/l) | 30° C. |
| 8 | Tryptone (10 g/l), plus yeast extract (1 g/l) and Sal-glc (80 mg/l) | 30° C. |
| 9 | Tryptone (10 g/l), plus yeast extract (1 g/l) and | 26° C. |
| 10 | Tryptone (10 g/l), plus yeast extract (1 g/l) | 35° C., with $CO_2$ |

The following table shows the results for the four organisms tested on each batch of medium. Based on these results, it appears that incubation at 30° C. and 26° C. provide equivalent results, with both of these being slightly better for clearing than incubation at 35° C. in elevated $CO_2$. Glutamic acid was found to promote color of *P. aeruginosa* and *K. pneumoniae*, whereas yeast extract was detrimental to color production by these organisms.

Because inclusion of tryptophan was very beneficial, it was decided to test inclusion of another aromatic amino acid, phenylalanine. In this experiment, phenylalanine was tested for any beneficial effects in the medium. The base medium consisted of agar (17 g/l), skim milk powder (16 g/l), NaCl (5 g/l), monosodium glutamate (2 g/l), tyramine HCl (250 mg/l), tryptophan (250 mg/l), Ind-$SO_4$ (250 mg/l), Ind-glc (250 mg/l), and $MnCl_2$ (50 mg/l). The base medium was divided into 2 batches. One batch was comprised of the base medium and proteose peptone #3 (3 g/l). The second test batch was comprised of the base medium, proteose peptone #3 (3 g/l), and phenylalanine (250 mg/l). After inoculation of each batch with *E. coli*, *S. choleraesuis*, *K. pneumoniae*, and *P. aeruginosa*, plates from both batches were incubated at 30° C.

Surprisingly, Inclusion of phenylalanine was beneficial for coloration of *K. pneumoniae*, *P. aeruginosa* and *P. mirabilis*.

EXAMPLE 15

Effectiveness of Magnesium and Various Amino Acids

In this experiment, magnesium and various amino acids were tested with an aim toward enhancing the arylsulfatase reaction of *K. pneumoniae*, and the production of pyocyanin production by *P. aeruginosa*.

The base medium consisted of agar (17 g/l), skim milk powder (16 g/l), soy peptone (6 g/l), monosodium glutamate (2 g/l), urea (500 mg/l), tryptophan (250 mg/l), phenylalanine (250 mg/l), tyramine HCl (250 mg/l), Ind-$SO_4$ (250 mg/l), Sal-glc (70 mg/l), and $MnCl_2$ (50 mg/l). Following inoculation and incubation with organisms, the reactions were observed. The following table lists the various compounds tested.

TABLE 23

| Batch | Compound Tested |
|---|---|
| 1 | Control |
| 2 | $MgCl_2$ (500 mg/l) |

TABLE 22

| Batch | *E. coli* | *S. choleraesuis* | *K. pneumoniae* | *P. aeruginosa* |
|---|---|---|---|---|
| 1 | White; Clear Zone | Very Slightly Yellow | Medium Gray; Clear | Turquoise |
| 2 | White; Clear Zone | White | Light Gray; Clear | Yellow-Turquoise |
| 3 | White; Less Clear Zone | Slightly Yellow | Very Light Gray; Clear | Turquoise |
| 4 | White; Less Clear Zone | White | Very Light Gray; Less Clear | Yellow-Turquoise |
| 5 | White; Clear Zone | White | Light Gray; Clear | Light Turquoise |
| 6 | White; Less Clear Zone | White | Light Gray; Less Clear | Very Light Turquoise |
| 7 | White; Less Clear Zone | White | Medium Gray; Less Clear | Light Turquoise |
| 8 | Red/Clear Zone | White | Light Gray; Clear | Very Light Turquoise |
| 9 | White; Clear Zone | Slightly Yellow | Very Light Gray; Clear | Very Light Turquoise |
| 10 | White; Less Clear Zone | White | Very Light Gray; Less Clear | Very Light Turquoise |

EXAMPLE 14

Effect of Phenylalanine

TABLE 23-continued

| Batch | Compound Tested |
|---|---|
| 3 | Monosodium Glutamate (1 g/l) |
| 4 | Glutamine (1 g/l) |
| 5 | Monosodium Asparatate (1 g/l) |
| 6 | Proline (1 g/l) |
| 7 | Glycyl-Glutamate (1 g/l) |
| 8 | Acetamide (1 g/l) |

Of these additions, both $MgCl_2$ (batch 2) and glutamine (batch 4) enhanced pyocyanin production, although $MgCl_2$ slightly stimulated swarming by *P. mirabilis*. Additional glutamate (batch 3) had little effect. Aspartate, proline and acetamide (batches 5, 6 and 8) slightly decreased pyocyanin production. Surprisingly, glycyl-glutamate (batch 7) solubilized the casein and caused the entire plate to clear.

EXAMPLE 16

Effectiveness of Other Amino Acids

In this experiment, the effects of various other amino acids were tested with an aim toward enhancing the arylsulfatase reaction of *K. pneumoniae* and the production of pyocyanin by *P. aeruginosa*. The base medium consisted of agar (17 g/l), skim milk powder (16 g/l), soy peptone (6 g/l), $MgCl_2$ (1 g/l), monosodium glutamate (2 g/l), glutamine (1 g/l), tryptophan (500 mg/l), phenylalanine (250 mg/l), tyramine HCl (250 mg/l), Ind-$SO_4$ (250 mg/l), and Sal-glc (70 mg/l). The following table lists the compounds tested and the reactions observed following inoculation and incubation.

TABLE 24

| Batch | Compound Tested | Observation |
|---|---|---|
| 1 | None | *P. mirabilis* is light orange |
| 2 | L-Alanine | No effect |
| 3 | L-Histidine HCl | *P. mirabilis* is dark rust color, but swarms more |
| 4 | L-Lysine HCl | *P. mirabilis* swarms more |
| 5 | L-Ornithine HCl | *P. mirabilis* swarms more |
| 6 | L-Arginine HCl | *P. mirabilis* swarms more |
| 7 | L-Arginine base | *P. mirabilis* swarms more |

None of these amino acids had a notable beneficial effect for *K. pneumoniae* or *P. aeruginosa*, and most of them caused a slight increase in swarming by *P. mirabilis*.

Group VI

Comparison of Various Salts

In the next series of experiments, the effects of various salts on the swarming of Proteus were determined.

EXAMPLE 17

Comparison of NaCl And $Na_2SO_4$ With Other Variables

In this experiment, two base recipes were tested, comparing NaCl and $Na_2SO_4$ for their impact on the chromogenic and clearing reactions and their ability to induce swarming by *P. mirabilis*. Recipe 1 was used in batches 1 through 10, while recipe 2 was used in batches 11–19. Recipe 1 consisted of agar (17 g/l), skim milk powder (16 g/l), Marcor soy peptone (6 g/l), monosodium glutamate (2 g/l), tryptophan (250 mg/l), phenylalanine (250 mg/l), tyramine HCl (250 mg/l), Ind-$SO_4$ (250 mg/l), Sal-glc (70 mg/l), $MnCl_2$ (50 mg/l), and NaCl (5 g/l).

Recipe 2 was the same as recipe 1, except $Na_2SO_4$ (5 g/l) was used instead of NaCl. The media were divided into batches and varying concentrations of chemicals were added as shown in the following table.

TABLE 25

| | |
|---|---|
| 1 | Recipe 1 |
| 2 | Urea (500 mg/l) |
| 3 | Glutamine (1 gl) |
| 4 | $MgCl_2$ (1 g/l) |
| 5 | $CuSO_4$ (50 mg/l) |
| 6 | Tryptophan (250 mg/l) |
| 7 | Glucuronamide (1 g/l) |
| 8 | Lactose (5 g/l) |
| 9 | Tryptophan (250 mg/l), $CuSO_4$ (50 mg/l), Glutamine (1 g/l), $MgCl_2$ (1 g/l) |
| 10 | Tryptophan (250 mg/l), $CuSO_4$ (50 mg/l), Glutamine (1 g/l), $MgCl_2$ (1 g/l), Urea (500 mg/l) |
| 11 | Recipe 2 |
| 12 | Urea (500 mg/l) |
| 13 | Glutamine (1 g/l) |
| 14 | $MgCl_2$ (1 g/l) |
| 15 | $CuSO_4$ (50 mg/l) |
| 16 | Tryptophan (250 mg/l) |
| 17 | Glucuronamide (1 g/l) |
| 18 | Lactose (5 g/l) |
| 19 | Tryptophan (250 mg/l), $CuSO_4$ (50 mg/l), Glutamine (1 g/l), $MgCl_2$ (1 g/l) |
| 20 | Tryptophan (250 mg/1), $CuSO_4$ (50 mg/l), Glutamine (1 g/l), $MgCl_2$ (1 g/l), Urea (500 mg/l) |

In general, plates made with $Na_2SO_4$ (batches 11–20) showed less swarming by *P. mirabilis* and slightly sharper zones of cling around *E. coli*, *K. pneumoniae* and *E. faecalis*, than plates made with NaCl (batches 1–10). Plates with added $CuSO_4$ (batches 5 and 15) exhibited greatly reduced swarming. Thus, it appears that chloride ions stimulate swarming more than sulfate ions.

EXAMPLE 18

Comparison of Magnesium Chloride and Magnesium Sulfate, Along With Manganese Sulfate and Copper Sulfate In this example, chloride and sulfate salts of magnesium were compared along with various concentrations of $CuSO_4$ and $MnSO_4$ for their appropriateness for inclusion in the medium, and their ability to minimize swarming by *P. mirabilis*. The base medium consisted of agar (17 g/l), skim milk powder (16 g/l), Marcor soy peptone (6 g/l), $Na_2SO_4 \cdot H_2O$ (5 g/l), monosodium glutamate (2 g/l), glutamine (1 g/l), tryptophan (500 mg/l), phenylalanine (250 mg/l), tyramine HCl (250 mg/l), Ind-$SO_4$ (250 mg/l), and Sal-glc (70 mg/l). The medium was divided into 10 batches and varying concentrations of minerals were added as shown in the following table

TABLE 26

| Batch | $MgSO_4$ Conc. | $MgCl_2$ Conc. | $MnSO_4$ Conc. | $CuSO_4$ Conc. |
|---|---|---|---|---|
| 1 | — | 1 g/l | 50 mg/l | 50 mg/l |
| 2 | 1.25 g/l | | 50 mg/l | 50 mg/l |
| 3 | 1.25 g/l | | 50 mg/l | 0 mg/l |
| 4 | 1.25 g/l | | 50 mg/l | 25 mg/l |
| 5 | 1.25 g/l | | 50 mg/l | 75 mg/l |
| 6 | 1.25 g/l | | 50 mg/l | 100 mg/l |
| 7 | 1.25 g/l | | 0 mg/l | 50 mg/l |
| 8 | 1.25 g/l | | 25 mg/l | 50 mg/l |
| 9 | 1.25 g/l | | 75 mg/l | 50 mg/l |
| 10 | 1.25 g/l | | 100 mg/l | 50 mg/l |

Batch 2 ($MgSO_4$) was better than 1 ($MgCl_2$), since Proteus swarmed more on batch 1. This observation confirmed the finding in the previous example, that chloride stimulates swarming by *P. mirabilis* more than sulfate. Also, Klebsiella and Pseudomonas were colored darker on batch 2 in comparison with batch 1. The clearing around *E. coli* and *E. faecalis* was more distinct on batch 1, as compared to batch 1. The $CuSO_4$ inhibited the swarming of Proteus and made the colonies a little darker. However, the Klebsiella colonies were a little lighter with $CuSO_4$. Of these batches, 2 and 3 provided the best overall results. Based on these results, it was determined that sulfate salts were preferable to chloride salts. There is a fairly broad range of concentrations for Mn and Cu that are effective. However, Mn gave slightly better coloration and a concentration of 50 mg/l appeared to be close to optimal.

Group VII

Effect of Peptones on Chromogenic Reactions and Organism Growth

In this group of experiments the effects of various peptones and extracts on the chromogenic reactions was studied. The selection of specific growth substances had a profound effect on many of the chromogenic reactions. It was found that the overall medium could be greatly improved by the judicious selection of peptones.

EXAMPLE 19

Effect of Various Peptones

In this experiment, the effects of various peptones were studied. The base medium consisted of agar (17 g/l), skim milk powder (16 g/l), NaCl (5 g/l), monosodium glutamate (2 g/l), Ind-$SO_4$ (250 mg/l), Ind-glc (250 mg/l), tyramine HCl (250 mg/l), tryptophan (250 mg/l), and $MnCl_2$ (50 mg/l). The base medium was divided into 26 batches and various compounds were added, as shown in the following table. Two lots of proteose peptone #3 were tested in this example, with one lot designated as "old" and the other as "new." The designation "CAA" is used in reference to casamino acids commercially available from Marcor; "CE90" is a pancreatic digest of casein, commercially available from Deltown; and GP Mix is a proprietary mixture produced by Biolog, Inc.

TABLE 27

| Batch | Compounds Added |
|---|---|
| 1 | 3 g/l Proteose Peptone #3 (old) |
| 2 | 6 g/l Proteose Peptone #3 (old) |

TABLE 27-continued

| Batch | Compounds Added |
|---|---|
| 3 | 3 g/l Proteose Peptone #3 (new) |
| 4 | 6 g/l Proteose Peptone #3 (new) |
| 5 | 3 g/l Proteose Peptone (new) |
| 6 | 3 g/l Proteose Peptone (new) plus 3 g/l Proteose Peptone #3 (old) |
| 7 | 3 g/l Proteose Peptone (Marcor) |
| 8 | 3 g/l Protease Peptone (Marcor), plus 3 g/l Proteose Peptone #3 (old) |
| 9 | 3 g/l CAA (Marcor) |
| 10 | 3 g/l CAA (Marcor), plus 3 g/l Proteose Peptone #3 (old) |
| 11 | 3 g/l CAA-R (Marcor) |
| 12 | 3 g/l CAA-R (Marcor), plus 3 g/l Proteose Peptone #3 (old) |
| 13 | 3 g/l Casein Peptone (Marcor) |
| 14 | 3 g/l Casein Peptone (Marcor), plus 3 g/l Proteose Peptone #3 (old) |
| 15 | 3 g/l CE90MX |
| 16 | 3 g/l CE90MX, plus 3 g/l Protease Peptone #3 (old) |
| 17 | 3 g/l TSB |
| 18 | 3 g/l TSB plus 3 g/l Proteose Peptone #3 (old) |
| 19 | 3 g/l Tryptose |
| 20 | 3 g/l Tryptose, plus 3 g/l Proteose Peptone #3 (old) |
| 21 | 3 g/l Tryptone |
| 22 | 3 g/l Tryptone, plus 3 g/l Proteose Peptone #3 (old) |
| 23 | 3 g/l Soy Peptone |
| 24 | 3 g/l Soy Peptone, plus 3 g/l Proteose Peptone #3 (old) |
| 25 | 3 g/l Pancreatic Digest of Gelatin |
| 26 | 3 g/l Pancreatic Digest of Gelatin, plus 3 g/l Proteose Peptone #3 (old) |

TABLE 28

| Batch | E. coli | S. choleraesuis | K. pneumoniae | P. aeruginosa | P. mirabilis | E. faecalis |
|---|---|---|---|---|---|---|
| 7, 8 | Gray; Clearing | Yellow | Light Gray; Partial Clearing | Turquoise | Orange; Poor Growth | White; Clearing |
| 9, 10 | Gray; Clearing | Yellow | Light Gray; Partial Clearing | Turquoise | Orange; Poor Growth | White; Clearing |
| 13, 14 | Gray; Clearing | More Yellow; Worse | Less Gray; Worse | Darker; Better | Better | White; Clearing |
| 17, 18 | Gray; Clearing | Less Yellow; Better | Darker; Better | Lighter; Worse | Better | White; Clearing |
| 19, 20 | Gray; Clearing | Less Yellow; Better | Darker; Better | Lighter; Worse | Better | White; Cleaning |
| 23, 24 | Slightly Darker; Better Growth | Less Yellow; Better | Darker; Better | Lighter; Worse | Better | White; Clearing |

Surprisingly, the amount and the type of specific peptones added had a very strong effect on the reactions produced by the bacteria. Of batches 1–8, batches 7 and 8 (Marcor PP) were best for *E. coli* and *P. aeruginosa*. Batches 1–4 were second best and batches 5 and 6 were the next best. Thus, based on these results 6 g/l peptone provided better results for *E. coli* and *P. aeruginosa* than 3 g/l peptone.

For *E. coli*, batch 23 (soy peptone), was best, followed by batch 17 (TSB) and batch 7 (Marcor PP). For *K. pneumoniae*, batch 17 (TSB) was best, followed by batch 23 (soy peptone), and batch 7 (Marcor PP). For *P. aeruginosa*, batch 13 (Marcor casein peptone) was best, followed by batches 9 (CAA), 7 (Marcor PP), and 19 (tryptose). Batch 25 (pancreatic digest of casein) produced the bluest colonies of all the above formulae. Other batches produced colonies that were slightly lighter turquoise or yellow-green. For *S. choleraesuis,* batches 15 (CE90 MX), and 25 (pancreatic digest of gelatin) were the best. For *P. mirabilis,* better growth was observed on batches 13 (casein peptone), 17 (TSB), and 23 (soy peptone). For *E. faecalis,* the results were all about the same except for batch 13 (casein peptone), which produced a little less clearing.

The indole spot tests with *E. coli* were negative for all of these formulae, although batch 17 (TSB) may produce a very weak positive result. The best plates and reactions for the tested organisms are shown in the previous table. Based on these results, the plates with the best overall reactions are batches 17 and 18 (TSB), along with batches 23 and 24 (soy peptone).

EXAMPLE 20

Defined Media and Peptones

In the previous example it was observed that soy peptones, perhaps in combination with casein peptones (as in TSB) were beneficial. In this example, the effects of soy and casein peptones were tested. The effects of these peptones on the spot indole test reaction was also observed.

The base medium was a defined composition comprised of agar (17 g/l), skim milk powder (16 g/l), NaCl (5 g/l), sodium glutamate (2 g/l), urea (500 mg/l) tyramine HCl (250 mg/l) tryptophan (250 mg/l), phenylalanine (250 mg/l), Ind-$SO_4$ (250 mg/l), Mag-glc (70 mg/l), and $MnCl_2$ (50 mg/l).

Various concentrations of soy and casein peptone at a ratio of 2:1, or soy peptone alone were added to the above base medium in order to produce 10 batches of media. In batches 1 through 5, soy and casein peptone were added at concentrations corresponding to a total of 6 g/l, 9 g/l, 12 g/l, 15 g/l, and 18 g/l respectively. Batches 6–10 contained the same concentrations of soy peptone alone.

Cultures of *E. coli, K. pneumoniae, P. aeruginosa, P. mirabilis,* and *E. faecalis* were inoculated on each of the above formulations and incubated at 30° C. The plates were then observed for colony color and morphology. Spot indole tests were also performed on *E. coli.*

Of the soy/casein plates, the 6 g/l concentration was the best. However, the coloration of the Pseudomonas colonies appeared too light on this medium. The soy peptone plates produced good results, although at the higher concentrations (15 g/l and 18 g/l) the Klebsiella colonies were a little too light in color. Of all the tested formulations, the one containing 6 g/l soy peptone produced the best results in terms of colony color and morphology and spot indole test results. With this formulation, *E. coli* colonies are red and the spot indole results are excellent. *K. pneumoniae* colonies are blue/black, *P. aeruginosa* colonies are turquoise, *P. mirabilis* is orange, and *E. faecalis* colonies are white with clear halos. Thus, based on these results, soy peptone at a concentration of 6 g/l to 9 g/l appears to be optimal for this medium.

EXAMPLE 21

Various Soy Peptones

In this experiment, the utility of various brands and lots of soy peptones was tested. The base medium consisted of agar (17 g/l), skim milk powder (16 g/l)), monosodium glutamate (2 g/l), glutamine (1 g/l), tryptophan (500 mg/l), phenylalanine (250 mg/l), tyramine (250 mg/l), Sal-glc (70 mg/l), Ind-$SO_4$ (250 mg/l), $MnCl_2$ (50 mg/l), and $CuSO_4$ (50 mg/l). The mixture was divided into 15 batches, and the various peptones listed in the following table were added. The designations "SE50M" and "SE50BT" are different grades of soy peptone, commercially available from Marcor. Hy Soy is a specific grade of soy peptone, commercially available from Sheffield Products, Norwich, N.Y. Unless otherwise indicated, each peptone was tested at 6g/l.

TABLE 29

| Batch | Peptone and Other Components |
|---|---|
| 1 | Marcor Soy Peptone MD-R6623 |
| 2 | Marcor Soy Peptone MD-R6623, with 500 mg/l Malt Extract |
| 3 | Marcor Soy Peptone MD-R6623, with 100 mg/l each of Serine, Methionine, Glycine, Thymidine, ad Hypoxanthine |
| 4 | Marcor Soy Peptone SE 50M 92-0934-02 |
| 5 | Marcor Soy Peptone SE 50M 92-0934-02, with 500 mg/l Malt Extract |
| 6 | Marcor Soy Peptone SE 50M 91-0126-01 |
| 7 | Marcor Soy Peptone SE 50M C703 (1987) |
| 8 | Marcor Soy Peptone SE 50BT B521 |
| 9 | Oxoid Soya Peptone |
| 10 | DIFCO Soytone |
| 11 | Sheffield HySoy |
| 12 | Marcor Proteose Peptone |
| 13 | Marcor Casein Peptone 4.5 g/l with Marcor Soy Peptone SE 50M 92-0934-02 (1.5 g/l) |
| 14 | Oxoid TSA |
| 15 | DIFCO TSA |

Of these batches, 1, 2, 7 and 11 were the best. Malt extract (batch 2) did not produce any significantly different results. While *K. pneumoniae* colonies looked good on batches 9 and 10, these formulations enhanced the swarming of Proteus, making them less useful. Batch 12 was not good for *K. pneumoniae* and Proteus swarmed on this medium. Batch 11 was good, although the Pseudomonas colonies were colored a little lighter. The use of serine, methionine, thymidine, and hypoxanthine (batch 3) produced results that were slightly worse. Neither the TSA recipes (batches 14 and 15) nor the SE 50 BT (batch 8) produced good results.

For *K. pneumoniae,* the best plates were from batches 11, 15, 12, 7 and 2, listed in order of best to worst. For Pseudomonas, plates from batches 13, 12 and 8 were best. The swarming of Proteus was especially bad in batches 13, 12, 10 and 9 (listed in order of worst to best).

EXAMPLE 22

Use of Different Soy Peptones

In this example, additional commercially available soy peptones from various manufacturers were tested. The base medium consisted of agar (17 g/l), skim milk powder (16 g/l), $NaSO_4$ (anhydrous)(2.5 g/l), $MgSO_4$ (1.25 g/l), monosodium glutamate (2 g/l), glutamine (1 g/l), tryptophan (500 mg/l), phenylalanine (250 mg/l), tyramine HCl (250 mg/l), Ind-$SO_4$ (250 mg/l), Sal-glc (70 mg/l), and $MnSO_4$ (50 mg/l). The mixture was divided into 10 batches, and the various soy peptones listed in the following table were tested. Unless otherwise indicated, each peptone was tested at 6 g/l.

TABLE 30

| Batch | Soy Peptone |
|---|---|
| 1 | Marcor MD-R6623 |
| 2 | Marcor HS MD-00583 |
| 3 | Marcor HS MD-06851 |
| 4 | Deltown L217 |
| 5 | Champlain CVP-LS |
| 6 | Champlain Pansoy M |

TABLE 30-continued

| Batch | Soy Peptone |
|---|---|
| 7 | Champlain Pansoy 61 |
| 8 | Sheffield Hy-Soy |
| 9 | Sheffield NZ-Soy |
| 10 | Sheffield Ami-Soy |

Of the various soy peptones tested, batches 2 (Marcor HS MD-00583) and 8 (Sheffield Hy-Soy) provided the best results, while batch 1 also produced very good results. The results produced in batch 4 were similar to those obtained for batch 1, although Pseudomonas colonies were slightly lighter and the Proteus swarmed more on batch 4. Batch 3 produced *K. pneumoniae* colonies that were too light and Salmonella colonies that were too dark.

Batches 5 and 6 produced very interesting results. Batch 5 was a darker colored medium than the other batches. On this medium, the Klebsiella and Pseudomonas colonies were very dark and the Salmonella colonies were darker than on the other media. Also, *P. mirabilis* did not swarm on this batch. However, there was no clearing around the *E. coli* and *E. faecalis* colonies, somewhat limiting the usefulness of this formulation.

On batch 6, Pseudomonas colonies were very yellow. However, there was poor growth of *P. mirabilis* and the colonies were not colored. Klebsiella colonies were likewise colorless. In addition, there was no clearing around the *E. coli* and *E. faecalis* colonies. The Pseudomonas color is intensified on this agar, but is yellow rather than green.

Batch 7 was satisfactory, although the Klebsiella colonies were light colored and *P. mirabilis* swarmed more. Batch 9 produced colonies of *P. mirabilis* and Pseudomonas that were light colored, although the Salmonella colonies were darker. However, the Klebsiella colonies were not colored and there was poor clearing around the *E. coli* and *E. faecalis* colonies. Like batch 5, batch 10 was a darker medium and the reactions were similar on these media. However, the Klebsiella colonies were not colored.

Based on these results, it was determined that the soy peptones used in batches 2 and 8 were optimal.

Group VIII

Optimization of Peptones, Extracts, and Amino Acids for Growth of Staphylococcus, and Stabilization of the Indole Spot Test In view of their common association with UTI's, it is important that a culture medium be designed to permit isolation and identification of Staphylococcus species, particularly *S. aureus* and *S. saprophyticus*. In the course of these experiments, it was observed that staphylococci did not grow well on media containing only soy peptone. Therefore, other peptones, extracts and infusions were tested and compared.

In this set of experiments, the optimization of base nutrients to produce the best growth of Staphylococcus, while producing strong spot indole tests by *E. coli* was investigated.

EXAMPLE 23

Peptone Composition and Reactions

In this experiment, the impact of different peptones, extracts and infusions was tested when added to a base medium comprising agar (17 g/l), skim milk powder (16 g/l), soy peptone (6 g/l), $Na_2SO_4$, anhydrous (2.5 g/l), $MgSO_4$, anhydrous (0.6 g/l), monosodium glutamate (2 g/l), glutamine (1 g/l), tryptophan (500 mg/l), phenylalanine (250 mg/l), tyramine (200 mg/l), Ind-$SO_4$ (250 mg/l), Sal-glc (70 mg/l), and $MnSO_4$ (50 mg/l). This medium was divided into 20 batches and various additions were made as shown in the following table. Each batch was then inoculated with *E. coli, K. pneumoniae, P. aeruginosa, S. aureus, S. saprophyticus,* and group B streptococci. Following incubation, the relative amount of growth compared to the control batch, and spot indole test results were recorded for each batch.

TABLE 31

| Batch | Added Compound | Indole Reaction | Better Results | Worse Results |
|---|---|---|---|---|
| 1 | Control | Very Weak | | |
| 2 | Soy Peptone (3 g/l) | Strong Positive | *P. aeruginosa, K. pneumoniae, S. aureus* | |
| 3 | Oxoid Yeast Extract (1 g/l), plus Beef Heart Infusion (1 g/l) | Negative | *K. pneumoniae,* Group B strep, *S. aureus, S. saprophyticus* | |
| 4 | Oxoid Yeast Extract (1 g/l) | Very Weak | *K. pneumoniae, S. saprophyticus,* | |
| 5 | Oxoid Yeast Extract (3 g/l) | Very Weak | *K. pneumoniae, S. aureus, S. saprophyticus* | *E. coli* |
| 6 | Beef Heart Infusion (1 g/l) | Very Weak | *S. aureus* | |
| 7 | Beef Heart Infusion (3 g/l) | Very Weak | *K. pneumonias,* Group B strep, *S. aureus, S. saprophyticus* | |
| 8 | Brain Heart Infusion (1 g/l) | Very Weak | *K. pneumoniae, S. aureus, S. saprophyticus* | |
| 9 | Brain Heart Infusion (3 g/l) | Positive | *K. pneumoniae,* Group B strep, *S. aureus, S. saprophyticus* | |
| 10 | Marcor Proteose Peptone (1 g/l) | Very Weak | *K. pneumoniae,* Group B strep, *S. aureus, S. saprophyticus* | |
| 11 | Marcor Proteose Peptone (3 g/l) | Very Weak | *K. pneumoniae,* Group B strep, *S. aureus, S. saprophyticus* | |
| 12 | Oxoid Lab Lemco (1 g/l) | Very Weak | *K. pneumoniae,* Group B strep | |

TABLE 31-continued

| Batch | Added Compound | Indole Reaction | Better Results | Worse Results |
|---|---|---|---|---|
| 13 | Oxoid Lab Lemco (3 g/l) | Negative | *K. pneumoniae*, Group B strep, *S. aureus*, *S. saprophyticus* | |
| 14 | Casein Peptone (1 g/l) (Oxoid Peptonized Milk) | Very Weak | *S. saprophyticus* | |
| 15 | Casein Peptone (3 g/l) (Oxoid Peptonized Milk) | Very Weak | *S. aureus, S. saprophyticus* | *P. aeruginosa, E. faecalis* |
| 16 | Fish Peptone, Low Salt (1 g/l) (U.S. Biochemical) | Strong Positive | *K. pneumoniae*, Group B strep, *S. aureus*, *S. saprophyticus* | *P. aeruginosa* |
| 17 | Fish Peptone, Low Salt (3 g/l) (U.S. Biochemical) | Strong Positive | *K. pneumoniae*, Group B strep, *S. aureus*, *S. saprophyticus* | *P. aeruginosa* |
| 18 | Mannitol (1 g/l) | Weak | | *P. aeruginosa* |
| 19 | Mannitol (3 g/l) | Positive | | *P. aeruginosa* (very bad) |
| 20 | Soluble Starch (1 g/l) | Very Weak | *S. saprophyticus* | *P. aeruginosa* |

Based on these results, it was apparent that the peptone included within media strongly affects the indole reaction, as well as the coloration, reaction with casein, and growth of these organisms. Additional soy peptone, fish peptone, and brain heart infusion produced the best results (batches 2, 9, 16 and 17).

The fish peptone had one negative feature in that it decreased the green coloration of *P. aeruginosa*. Overall, brain heart infusion (batch 9) was best, as it gave the strongest coloration, growth and casein reactions, particularly with the gram-positive bacteria

EXAMPLE 24

Soy Peptone With and Without BHI and Growth of Staphylococcus

In this experiment, the effects of various soy peptone concentrations and brain heart infusion (BHI) concentrations on the spot indole reaction, growth and proteolysis of *S. aureus* and *S. saprophyticus,* and swarming of *P. mirabilis* were tested. The base medium was the same as in the previous example, with the addition of 6 g/l soy peptone. Additional ingredients were added as shown in the table below.

TABLE 32

| Batch | Additional Ingredients | Important Observations |
|---|---|---|
| 1 | Control (6 g/l Soy Peptone) | |
| 2 | 3 g/l Soy Peptone | |
| 3 | 6 g/l Soy Peptone | *K. pneumoniae* darker; *S. aureus* and *S. saprophyticus* grew better than on batch 1 (control). |
| 4 | 9 g/l Soy Peptone | Same as batch 3. |
| 5 | 1 g/l Soy Peptone, plus 1 g/l BHI | |
| 6 | 2 g/l Soy Peptone, plus 2 g/l BHI | |
| 7 | 3 g/l Soy Peptone, plus 3 g/l BHI | *K. pneumoniae* darker; *S. aureus* and *S. saprophyticus* grew better than on batch 1 (control). |
| 8 | 4 g/l Soy Peptone, plus 4 g/l BHI | *K. pneumoniae* even darker, *S. aureus* and *S. saprophyticus* grew better and exhibited better clearing than on batch 1 (control); *P. aeruginosa* was lighter. |
| 9 | 3 g/l Soy Peptone, plus 1 g/l BHI | |
| 10 | 4 g/l Soy Peptone, plus 2 g/l BHI | |
| 11 | 3 g/l BHI | *K. pneumoniae* light |

Based on these results, it appeared that the soy peptone concentration could be raised to at least 12 g/l. The growth of the staphylococci were best with BHI at 3 g/l (batches 7 and 11), and it appears to improve the proteolytic clearing produced by these organisms. Of note was the observation that Proteus did not swarm on batches 1 or 11. With increasing soy peptone concentrations, Proteus swarming increased. All batches provided strong indole reactions with *E. coli.*

As the soy peptone level was increased, swarming by *P. mirabilis* also increased, but the swarming was still within reason. Of these batches, numbers 3, 4, and 8 were good, while batches 7 and 11 were best. The optimal mount of BHI therefore, appears to be around 3 g/l and the optimal amount of soy peptone appears to be around 6 g/l to 9 g/l.

EXAMPLE 25

Varying Concentrations of Sal-Glc With Methyl-glc; Beef Powder v. BHI; and Increased Phenylalanine In this experiment, the use of various compounds to stabilize the spot indole test was studied. The base medium consisted of agar (17 g/l), soy peptone (Hy Soy) (9 g/l), $Na_2SO_4$, anhydrous (2.5 g/l ), $MgSO_4$, anhydrous (0.6 g/l), tryptophan (500 mg/l), phenylalanine (250 mg/l), glutamine (1 g/l), tyramine (200 mg/l), $Ind-SO_4$ (250 mg/l), methyl-glc (70 mg/l), and MnSO$_4$ (50 mg/l). The following table lists the components added in each batch.

TABLE 33

| Batch | Added Ingredients |
|---|---|
| 1 | Sal-glc (70 mg/l), plus Intergen Beef Powder (3 g/l) lot #12342 |
| 2 | Sal-glc (70 mg/l), plus intergen Beef Powder (3 g/l) lot #LT63106 |
| 3 | Sal-glc (70 mg/l), plus Intergen Beef Powder (5 g/l) lot #LT63106 |
| 4 | Sal-glc (70 mg/l), plus BHI (3 g/l), plus 250 mg phenylalanine |
| 5 | Sal-glc (70 mg/l), plus BHI (3 g/l) |
| 6 | Sal-glc (30 mg/l), plus BHI (3 g/l) |
| 7 | Sal-glc (40 mg/l), plus BHI (3 g/l) |
| 8 | Sal-glc (50 mg/l), plus BHI (3 g/l) |
| 9 | Sal-glc (60 mg/l), plus BHI (3 g/l) |
| 10 | Sal-glc (140 mg/l), plus BHI (3 g/l) |

On batch 1 there was weak growth with *S. aureus*. On batch 2, *S. aureus* was a little more yellow in color. The results with batch 3 were about the same as batch 2. Batches 4 and 5 were equivalent, with pink coloration of *E. coli*. The coloration of *E. coli* was white on batch 6, light pink on batches 7, 8 and 9, and dark red on batch 10. Thus, the methyl-glc did not enhance *E. coli* coloration. A Sal-glc concentration of 70 mg/l was satisfactory, but 140 mg/l was clearly better.

In addition, plates from batches 1 to 5 of the above prepared media were stored for approximately one month, and then inoculated with the standard *E. coli* strain (ATCC type strain, #11775), as well as five clinically isolated *E. coli* strains. After incubation, the spot indole reaction was tested and recorded for each strain. For batches 1, 2, 4 and 5, all five strains produced very light indole reactions. Batch 3 produced strong results for three strains; the reaction was weaker for the other three strains. A control plate of TSA was also used; the indole reaction from all six strains was strong on this medium.

It was also observed that the red glucuronidase reaction was faded to pink in batches 1 through 5. These results indicate that Intergen beef powder is better in maintaining the spot indole test when it is at a concentration of 5 g/l rather than 3 g/l.

EXAMPLE 26

Stability of Spot Indole Reactions

In this experiment, ways to prolong the indole test shelf life of prepared media were investigated. The base medium consisted of agar (17 g/l), Hy Soy soy peptone (9 g/l), BHI (3 g/l), Na$_2$SO, anhydrous (2.5 g), MgSO$_4$, anhydrous (0.6 g/l), tryptophan (500 mg/l), phenylalanine (250 mg/l), tyramine (200 mg/l), Ind-SO$_4$ (250 mg/l), Sal-glc (70 mg/l), and MnSO$_4$ (50 mg/l). The following table shows the ingredients added to each of the ten batches tested. Also included in this table are the notable observations following inoculation of organisms and incubation for 24 hours.

TABLE 34

| Batch | Compounds Added | Observations |
|---|---|---|
| 1 | Control (no glutamate, no glutamine) | |
| 2 | 500 mg/l tryptophan | *P. aeruginosa* slightly darker, *S. aureus* very slightly more yellow |
| 3 | 1 g/l glutamine | *P. aeruginosa* slightly darker; *S. aureus* slightly more yellow and with better growth |
| 4 | 2 g/l glutamate | *P. aeruginosa* more yellow; *S. aureus* less yellow |
| 5 | 100 mg/l methylglucuronide | Same as the control |
| 6 | 500 mg/l methylglucuronide | Same as the control although *K. pneumoniae* slightly darker |
| 7 | 3 g/l Primex fish peptone (08/200) | Less clearing by *E. coli* and *S. saprophyticus*; better growth of *S. aureus* |
| 8 | 3 g/l Primex fish peptone (08/300) | Slightly less clearing by *S. saprophyticus*; better growth of *S. aureus* |
| 9 | 3 g/l Intergen beef powder | Slightly less clearing by *S. saprophyticus*; better growth of *S. aureus*; *K. pneumoniae* slightly darker |
| 10 | 3 g/l Quest Primatone beef extract | Slightly less clearing by *S. saprophyticus*; better growth of *S. aureus*; *K. pneumoniae* slightly darker, *P. aeruginosa* lighter |

Of the above formulations, batches 3, 6 and 9 were the best. The indole reaction of *E. coli* was first tested using freshly prepared plates. Batches 1, 5, 6 and 7 produced weaker reactions, and batch 2 produced a stronger indole reaction. Batch 4 gave a slight deterioration of color for *P. aeruginosa* and *S. aureus*.

The plates were then stored under refrigeration and retested after two weeks. The type strain (ATCC #11775) and five clinical isolates of *E. coli* characterized as weak indole positive organisms were tested. The following table shows the results obtained for these plates. A control plate of TSA and blood was also used (batch 11). In the following table, "w" indicates a weak reaction; "+" indicates a positive test result; and ND indicates that the test was not conducted.

TABLE 35

| Batch | Glucuronidase Test E. coli, Type Strain | Spot Indole Test E. coli, Type Strain | Five Clinical E. coli Isolates |
|---|---|---|---|
| 1 | w | Faint Blue | Faint Blue |
| 2 | w | Faint Blue | Faint Blue |
| 3 | w | Faint Blue | Three Faint Blue; One Medium Blue; One Dark Blue |
| 4 | + | Dark Blue | Three Light to Faint Blue; Two Medium Blue |
| 5 | + | Faint Blue | Four Light to Faint Blue; One Medium Blue |
| 6 | + | Faint Blue | Four Light to Faint Blue; One Medium Blue |
| 7 | w | Faint Blue | Four Light to Faint Blue; One Medium Blue |
| 8 | ND | ND | ND |
| 9 | + | Faint Blue | Four Light to Faint Blue; One Medium Blue |
| 10 | w | Faint Blue | Four Light to Faint Blue; One Medium Blue |
| 11 | ND | Dark Blue | One Medium Blue; Four Dark Blue |

Based on these results, it appears that glutamate, methyl-glc, and Intergen beef powder prevent deterioration of the glucuronidase test over time. Surprisingly, glutamate prevented deterioration of the indole reaction in three out of six E. coli strains and glutamine prevented deterioration in two out of six E. coli strains.

EXAMPLE 27

Addition of Beef Extract and Other Compounds to Improve Shell Life of Medium

This experiment was designed to identify a way to improve the shelf life of the medium by adding more beef extract or other compounds. The base medium consisted of agar (17 g/l), skim milk powder (16 g/l), Hy Soy soy peptone (9 g/l), $Na_2SO_4$, anhydrous (2.5 g/l), $MgSO_4$, anhydrous (0.6 g/l), tryptophan (500 mg/l), phenylalanine (250 mg/l), glutamine (1 g/l), tyramine (200 mg/l), Ind-$SO_4$ (250 mg/l), Sal-glc (70 mg/l), and $MnSO_4$ (50 mg/l). The medium was divided into 12 batches, each containing the ingredients shown in the following table.

TABLE 36

| Batch | Added Compound(s) | Observations |
|---|---|---|
| 1 | 0.5% Intergen beef powder, with 0.8% kaolin (instead of skim milk) | Excellent for all except Klebsiella and gram-positives |
| 2 | 0.3% BHI | Excellent |
| 3 | 0.5% BHI | K. pneumoniae and P. aeruginosa darker, Proteus swarms more |
| 4 | 0.3% Marcor beef extract powder | Excellent |
| 5 | 0.5% Marcor beef extract powder | K. pneumoniae, are P. aeruginosa weaker, Proteus swarms more |
| 6 | 0.3% Intergen beef powder | P. aeruginosa weaker |
| 7 | 0.5% Intergen beef powder | P. aeruginosa good |
| 8 | 0.7% Intergen beef powder | P. aeruginosa good; K. pneumoniae a little darker |
| 9 | 0.9% Intergen beef powder | P. aeruginosa good, K. pneumoniae a little darker |
| 10 | 0.5% Intergen beef powder, plus 0.2% Na glutamate | P. aeruginosa a little lighter, K. pneumoniae a little darker |
| 11 | 0.5% Intergen beef powder, plus 0.4% Na glutamate | Not as good as batch 10 |
| 12 | 0.5% Intergen, plus 0.1% CVPLS (Champlain) | Possibly beneficial for K. pneumoniae and P. aeruginosa, but Proteus swarms more |

For E. coli, all of the batches were good, but the Marcor beef extract was a little weaker. The best formulations for K. pneumoniae were batches 2, 8, 9, 10, and 12. The next best group included 2, 3, 7, and 9. The worst formulations for this organism was batch 1. For P. mirabilis, the best was batch 1, as there was no swarming in the presence of kaolin. There was moderate swarming on all other batches.

For P. aeruginosa, batch 1 was the best, as the kaolin made the colonies very blue. The next best batches were 2 and 4. The worst batches were 3, 5, and 11.

For S. aureus, batch 1 was the worst, as kaolin inhibits the growth of gram-positive organisms. Batches 5, 11, and 12 were also bad, producing white colonies, rather than yellow.

Based on the above observations, at an equivalent concentration of 0.3%, BHI is better at giving S. aureus a strong yellow color. However, Marcor beef extract powder produces almost the same results as BHI. On Intergen beef powder, *P. aeruginosa* is a weaker green, but is still green.

In addition, the formulations listed above were also tested to determine their shelf life based on the indole reactions after 12 days in refrigerated storage. After storage for 12 days, agar plates corresponding to each of the 12 batches above, were inoculated with various. *E. coli* strains and the indole test reactions were observed.

Dark blue indole reactions were observed for all *E. coli* strains on batch 1 containing kaolin, and the organisms grew as red colonies. For batches containing 1.6% skim milk (2, 3, 4, 5 and 6), the indole test for all of the *E. coli* strains was light blue, and the colonies were pink.

The results for batches 7 through 9 were virtually identical to those of batches 2–6, except that two of the five *E. coli* strains had darker blue indole reactions. Batches 10, 11 and 12 were the best of all the batches, as all of the five *E. coli* strains produced blue indole reactions. Based on these results, it is apparent that monosodium glutamate was effective at prolonging the shelf life of the indole spot test. CVPLS was effective as well, but it made the coloration of *P. aeruginosa* lighter. Substitution of kaolin for skim milk also was effective, but kaolin was inhibitory to the gram-positive bacteria.

EXAMPLE 28

Radiation Sterilization of Medium to Prolong Shelf Life

In this experiment the possibility of radiation sterilization of all components of the medium with the exception of the agar was investigated. This was based on the view that in commercial use, the medium might be easier to prepare if it could be provided to users as a presterilized powder. Since milk powder caramelizes and darkens when sterilized by autoclaving, it was hypothesized that radiation sterilization of the milk powder would be preferable. It was also thought that this might extend the shelf life of the indole spot test in prepared agar media.

The powder components needed for one liter of medium consisted of Darigold non-fat dry milk (Darigold, NFDM, high heat treatment, Seattle, Wash.) (16 g), Hy Soy soy peptone (9 g), Intergen Beef Powder (7 g), $Na_2SO_4$, anhydrous (2.5 g), $MgSO_4$, anhydrous (0.6 g), monosodium glutamate (2 g), glutamine (1 g), tryptophan (500 mg), phenylalanine (250 mg), tyramine free base (200 mg), Ind-$SO_4$ (250 mg), Sal-glc (70 mg), and $MnSO_4$ (50 mg). Aliquots of this powder were subjected to electron beam radiation at doses of 2.5, 3.0, 3.5, and 4.0 MRAD. To prepare the medium, agar (17 g) was added to one liter of water and autoclaved for 15 minutes at 121° C. Then, the irradiated powder was added aseptically to the sterilized agar, mixed well, and dispensed into sterile petri plates. The poured agar plates were stored under refrigeration, and tested at weekly intervals with various strains of bacteria.

Overall this medium and method of preparation were very satisfactory. There was a slight but noticeable detrimental effect if the medium components were subjected to too much radiation. This was seen as slightly lighter chromogenic reactions with *P. mirabilis* and *S. choleraesuis*, and with poorer clearing of milk by *E. coli*, *K. pneumoniae*, *E. faecalis*, *S. aureus*, and *S. saprophyticus*. Thus, the preferred level of radiation is 2.5 MRAD. This medium was tested beyond 9 weeks of storage and all of the chromogenic and clearing reactions as well as the indole spot test remained satisfactory.

Although this embodiment was found to be highly satisfactory, it may prove beneficial to make some changes. For example, the agar concentration may need to be decreased to 10 to 15 g/l depending on the source and gel strength. Sal-glc may be increased from 70 mg/l to 120 mg/l, as this will give a more rapid and a darker red color. However, Sal-glc is the most expensive component of the medium, so there is a cost versus color tradeoff that must be kept in mind. In addition, if the medium is sterilized by radiation, it may not be necessary to add monosodium glutamate to preserve the stability of the indole spot test. Finally, the source and the levels of the soy peptone and meat extract must be evaluated and adjusted on lot-to-lot basis.

Group IX

Development of Urease and Tellurite Spot Tests

In this experiment, methods for growing bacteria on the medium of the present invention and testing them for their reactions in spot urease, and tellurite reduction tests are described. Traditionally, the urease test is performed in an inconvenient "test tube" format, and the tellurite reduction test is performed on a specialized agar medium. However, a new approach was developed whereby these tests can be easily and conveniently conducted. Furthermore, the unique tests developed for use with the medium of the present invention may be substituted for the traditional tests.

As described in Example 9, attempts to include tellurite in the medium were unsuccessful. Attempts to include the urease test in the medium without interfering with other important tests (data not shown) were likewise unsuccessful as described in the Description of the Invention. Thus, an important goal was to determine whether the medium of the present invention presented any problems in these test reactions, or whether the medium provided advantages over commonly used media. In addition, easy to perform and unique testing methods for tellurite reduction and urease activity were developed.

EXAMPLE 29

Spot Test Development

In this experiment, rapid methods were developed for testing bacteria grown on the medium of the present invention for their reactions in spot urease and tellurite reduction tests.

Urease

It is desirable to have a quick and reliable way to confirm the identity of members of the Proteeae, such as *P. mirabilis* with a urease spot test. Traditionally, urease test media contain urea, buffers, and phenol red (e.g., Christensen's urea agar, Ewing's urea broth [urea R broth], and Stuart's urea broth; see e.g., MacFaddin, Media for the Isolation-Cultivation-Identification-Maintenance of Medical Bacteria, p. 821–827). Other commercially available formats include urea-impregnated test strips or swabs (e.g., from Remel). In the traditional test formats, the medium is inoculated with a heavy suspension of organisms and incubated at 35° C. Following 15 min., 30 min., 60 min., and four hours of incubation, the medium is observed. Urease positive organisms will produce a bright pink or red color in the medium, while urease-negative organisms do not produce a color change in the medium. These methods are not specific for the presence of urease, as they all rely on the demonstration of alkalinity in the medium.

Disadvantages of the media presently used include the use of peptones in the media which can lead to false positive results, due to protein hydrolysis and release of excessive amino acid residues which then raise the pH. Furthermore, Stuart's urea broth is highly buffered and may mask the urease activity of delayed urease positive organisms. Thus, this medium is generally useful only for the strongly urease positive members of the Proteeae. Also, all of these media require heavy inocula in order to provide reliable results without the above-noted limitations.

Thus, what was needed was a urea test method and medium which provide rapid, reliable results. After some experimentation, a satisfactory reagent was developed. This reagent comprises urea, m-cresol purple and dimethylglutaric acid dissolved in water. The present invention contemplates that these components can be successfully employed over a range of concentrations. However, in a preferred embodiment the concentrations were approximately 5% urea, 0.05% m-cresol purple and 0.05% dimethylglutaric acid dissolved in water. This orange solution was used to saturate a filter paper disk. A blunt-ended wooden applicator stick was then used to pick a colony of bacterial growth from the medium and transferred as a dot onto the saturated filter paper. With strongly urease positive organisms such as *P. mirabilis*, the dot rams bright purple in a few seconds. With weakly urease positive bacteria (e.g., *K. pneumoniae*) it rams purple within 10–30 minutes, and with urease negative bacteria (e.g., *E. coli, S. choleraesuis, P. aeruginosa, E. faecalis, S. aureus, S. saprophyticus,* and *S. agalactiae*), the spot remains orange. Thus, results are almost immediately available for the strongly urease positive organisms and within half an hour for the weaker urease producers.

Unlike the traditional methods which utilize phenol red as a pH indicator, the method developed in this Example uses m-cresol purple. Phenol red changes from yellow to red at a pH of approximately 7.4, whereas m-cresol purple changes from yellow to purple at a pH of approximately 8.2. Because it requires a more substantial pH change to yield a color change, m-cresol purple is less susceptible to false positive reactions than phenol red. This unique method and reagent provides a rapid way to test the production of urease by organisms grown on the medium of the present invention. It is also contemplated that this test method and reagent will be useful in conjunction with other microbiological media, including those which interfere with traditional urease test methods.

Tellurite

It is also desirable to have a quick and reliable way to confirm the identity of *E. faecalis* with a spot test for tellurite. Tellurite tolerance is traditionally tested using an agar medium containing 0.04% potassium tellurite (see e.g., R. R. Facklam and J. A. Washington, "*Streptococcus and related catalasepk -negative gram-positive cocci,*" in *Manual of Clinical Microbiology*, American Society for Microbiology, 5th ed. [1991] p. 252). Suspected Enterococcus species are inoculated onto the medium, incubated at 35° C. for up to 7 days and observed for the development of black colonies. This test relies on the growth of organisms in the presence of tellurite, a compound which is toxic to most species (i.e., during the development of the medium of the present invention, addition of tellurite to the medium, even at low concentrations, was empirically found to inhibit growth). Therefore, it was deskable to develop a rapid, easy-to-perform spot test which could be performed on colonies present on the medium of the present invention.

After some experimentation, an easy to perform method was developed in which a solution of tellurite salt in water is prepared and one or two drops of the solution placed on colonies suspected of being *E. faecalis*. Within approximately one hour of incubation at room temperature, *E. faecalis* colonies reduce the tellurite and turn black. While the present invention contemplates use of a range of tellurite concentrations and salts (e.g., potassium, sodium, etc.), a solution of approximately 1% potassium tellurite was used in a preferred embodiment.

As clearly shown by the above examples, the present invention provides a medium which is optimized for the presumptive differentiation of the organisms most commonly associated with UTI's. In addition to the low iron concentration useful for enhancement of pyocyanin production by *P. aeruginosa,* the present medium also contains tyramine, glutamate, glutamine, and phenylalanine to stimulate color production by *P. aeruginosa* and *K. pneumoniae.* The magnesium in the medium also stimulates pyocyanin production. The low chloride concentration diminishes the swarming of Proteus. The presence of tyramine and manganese gives the brown color to *S. choleraesuis* colonies and other strains which produce tyramine oxidase. The tyramine is also useful as an arylsulfatase inducer. In addition, tyramine stimulates pyocyanin production, facilitating differentiation of *P. aeruginosa.*

Importantly, in addition to the presumptive identifications which are possible based on colony observations, the medium of the present invention permits the use of spot tests using isolated colonies. Unlike other commonly used media, there is no inhibition of these spot test reactions. For example, spot indole and urease tests may be conducted from isolated colonies to confirm the presence of *E. coli* and Proteus, and to distinguish certain species of bacteria. The observation that hydrochloric acid (preferably at a concentration of approximately 2N), dropped onto green colonies suspected of being *P. aeruginosa* turns the colonies pink is another test which is facilitated by the present invention.

It is contemplated that other tests useful for identification and differentiation of bacterial species can and will also be used in conjunction with the medium of the present invention. For example, catalase, oxidase, PYR hydrolysis, esculin hydrolysis and other tests useful in differentiation of bacterial species may be used. It is not intended that the present invention be limited to the particular spot or other enzyme test systems disclosed in the above examples.

It is also contemplated that other agar substitutes such as the pectin based products disclosed in U.S. Pat. Nos. 4,241, 186 and 4,282,317 issued to Roth, hereby incorporated by reference, could be used in the present invention. Such substitutes may decrease the use of expensive chemicals and would also permit ready use of pour plate, rather than streak plate methods in situations where such methods are desirable. Such modifications will also facilitate use of this medium with water and other liquid samples, especially those of environmental origin.

It is further contemplated that the medium of the present invention will be used in various formats. For example, it is contemplated that the medium will be used in existing and innovative new configurations such as that used in the "Diaslide," as described by M. Rosenberg et al., "Initial testing of a novel urine culture device," J. Clin. Microbiol., 30:2686 (1992). "Diaslide" is a device which contains CLED and either MacConkey or EMB on each side of an immersible plastic paddle for the growth and semi-quantitative analysis of bacteria from urine samples. It is therefore contemplated that the medium of the present invention will be used in a similar format. It is also contemplated that the medium of the present invention will be useful in other forms, including broth and semi-solid preparations. Thus, it is not intended that the medium of the present invention be limited to a solid preparation dispensed in any particular format such as petri plates.

It is also contemplated that other opacity producing agents will be used in the medium of the present invention, either in combination with milk, or as alternatives. It is foreseen that synthetic or modified milk-like solutions or other opaque proteinaceous solutions or suspensions could be substituted for or added to the skim milk. Furthermore, although the proteolysis and lactose utilization reactions may not be observable, use of opaque inorganic materials including, but not limited to kaolin, other silicates, titanium oxide, and calcium carbonate provide many of the same advantages as milk.

It is further contemplated that in addition to the chromogenic substrates disclosed in the above Examples, other substrates will be utilized in the present invention. For example, it is contemplated that substrates with fluorogenic, or luminogenic components will also be utilized in the present invention. It is not intended that the present invention be limited to a particular substrate, whether it be chromogenic, fluorogenic, luminogenic, or any other type used in detection systems.

It is also contemplated that the colony colors will vary, depending upon the chromogenic compounds used. Here again, many chromogens are now commercially available and others will undoubtedly become available in the future. Thus, any combinations of enzyme substrates and colors can be used in the medium of the present invention.

It is further contemplated that the medium of the present invention will be useful for the growth and presumptive identification of organisms other than those included in the Examples provided. For example as discussed above, *Streptococcus agalactiae* (group B strep) grows as small, white colonies, with a halo of clearing due to proteolysis. *Aerococcus urinae* grows as pinpoint red colonies (i.e., β-glucuronidase positive) with no clearing. *Salmonella arizonae* (Salmonella subspecies 3) grows as large, red (i.e., β-glucuronidase positive) colonies with no clearing. *Corynebacterium renale* grows as small orange colonies with weak zones of clearing due to proteolysis. Thus, it is contemplated that the medium and method of the present invention will be useful for other organisms associated with UTI's, as well as organisms not associated with UTI's.

It is also contemplated that other enzyme test systems will be incorporated in the medium of the present invention. For example, it is foreseen that chromogenic substrates could be added for β-galactosidase, β-xylosidase, and C8-esterase which are respectively useful in identifying *E. coli*, Klebsiella and Enterobacter species (see e.g., J. L. Sepulveda, "Rapid presumptive identification of gram-negative rods directly from blood cultures by simple enzymatic tests," J. Clin. Microbiol., 28:177–181 [1990]) and Salmonella species (A-M Freydiere and Y. Gille, "Detection of salmonellae by using Rambach agar and by a C8 esterase spot test," J. Clin. Microbiol., 29:2357–2359 [1991]). Other useful chromogenic substrates may be employed, and the scope of the current disclosure is not limited to those named above.

It is further contemplated that the medium of the present invention may be both selective and differential. Such media will inhibit the growth of some organisms, but other important species that do grow will be made distinguishable. For example, to make the medium selective for gram-negative bacteria, compounds such as deoxycholate, sodium dodecyl sulfate, and bile salts can be included, in order to inhibit the growth of gram-positive bacteria. Alternatively, to make the medium selective for gram-positive bacteria, compounds such as phenylethyl alcohol, colistin, and nalidixic acid can be included, in order to inhibit the growth of gram-negative bacteria.

It is further contemplated that the medium of the present invention can be modified by substituting, either partially or completely, other arylsulfatase inducers for the tyramine included in a preferred embodiment of the present invention, including such compounds as octopamine, dopamine, and norepinephrine (See e.g. T. Harada and Y. Murooka, supra).

It is further contemplated that the medium of the present invention can be modified by changing the nutrient and salt composition. As described in the present disclosure, many options are satisfactory. For example, it has been found that copper and iron salts can be used in place of, or in addition to, manganese salts for generating chromogenic reactions for tryptophan and tyramine oxidase. Chloride salts could be substituted for sulfate salts (although Proteus species may swarm more). Many different combinations of peptones and extracts are satisfactory, although the preferred nutrients have been highly optimized.

It is also contemplated that various compounds may be useful in the spot urease and tellurite tests. For example, use of pH indicators other than m-cresol purple in the urease spot test is contemplated (e.g., phenol red, brom-cresol purple, cresol red, phenol red, xylenol blue, thymol blue, etc.), as is use of buffers other than dimethyl glutaric acid. In addition, other tellurite salts are contemplated for use in the tellurite test. For example, either sodium or potassium tellurite salts may be used, as well as other tellurite-containing compounds.

Finally, it is further contemplated that the medium of the present invention can be modified by omitting one or more of the useful components. This may be of particular benefit in applications where it is important to lower the cost of the medium. For example, in some applications it may not be necessary to distinguish all of the bacterial species described, and in that case a simplified and less expensive medium can be devised by omitting components that are not necessary. Thus, in water testing, where primarily "coliform" bacteria are of interest, the medium could be simplified by omitting or reducing the levels of glutamic acid, glutamine, phenylalanine, tyramine, Ind-$SO_4$, manganese chloride, magnesium sulfate, and sodium sulfate. Furthermore, a chromogenic substrate for β-galactosidase could be added in place of or in addition to the chromogenic substrate for β-glucuronidase.

From the above, it is clear that the present invention provides a highly useful medium for the rapid and reliable isolation and differentiation of various gram-negative, as well as gram-positive bacteria. It is also clear that the method of the present invention provides an easy to use method for the rapid and reliable differentiation of various bacteria. Of particular importance is the use of the present invention for the growth and differentiation of the most common UTI etiologic agents, especially *E. coli* and *P. mirabilis* (gram-negative) and *E. faecalis* (gram-positive). The medium of the present invention provides significant advantages over other media, as all organism grow well and are distinguishable from each other, as well as other bacterial species. The present invention therefore, fills a need for media which can provide rapid diagnostic answers and point to a particular treatment regimen based on the etiologic agent of a patient's infection, rather than simply treating the patient empirically, possibly with an inappropriate antimicrobial.

What is claimed is:

1. A medium for identification of bacterial colonies comprising i) at least one proteinaceous opaque compound; ii) two or more chromogenic substrates selected from the group comprising arylsulfatase substrates, galactosidase substrates glucuronidase substrates, tryptophan oxidase substrates, and tyramine oxidase substrates; and iii) a nutrient base.

2. The medium of claim 1, wherein said nutrient base comprises one or more compounds selected from the group comprising magnesium sulfate and sodium sulfate, and one or more mixtures selected from the group comprising soy peptone and meat extract.

3. The medium of claim 1, wherein said proteinaceous compound is a milk-derived preparation.

4. The medium of claim 1, wherein said chromogenic substrate is a glucuronidase substrate selected from the group comprising 6-chloro-3-indolyl-β-D-glucuronide and 5-bromo-6-chloro-3-indolyl-β-D-glucuronide.

5. The medium of claim 1, wherein said chromogenic substrate is indoxyl-3-sulfate.

6. The medium of claim 1, further comprising at least one amine selected from the group consisting of glutamine, glutamic acid, tryptophan, phenylalanine, tyramine, octopamine, dopamine and norepinephrine.

7. A medium for identification of bacterial colonies comprising, in amounts sufficient for growth and differentiation of said bacterial colonies: i) at least one chromogenic glucuronidase substrate, and ii) at least one chromogenic arylsulfatase substrate.

8. The medium of claim 7, wherein said opaque compound is non-proteinaceous.

9. The medium of claim 8, wherein said non-proteinaceous compound is selected from the group comprising silicates, carbonates, and oxides.

10. The medium of claim 7, wherein said opaque compound is proteinaceous.

11. The medium of claim 10, wherein said opaque compound is a milk-derived preparation.

12. The medium of claim 7, further comprising at least one coordinating compound selected from the group consisting of manganese, copper and iron.

13. The medium of claim 7, further comprising at least one amine selected from the group consisting of glutamine, glutamic acid, tryptophan, phenylalanine, tyramine, octopamine, dopamine and norepinephrine.

14. A medium for identification of bacterial colonies comprising, in amounts sufficient for growth and differentiation of said bacterial colonies: i) at least one casein-containing compound; ii) a chromogenic glucuronidase substrate; iii) a chromogenic arylsulfatase substrate, iv) at least one coordinating compound; and v) a gelling agent.

15. The medium of claim 14, wherein said chromogenic glucuronidase substrate is selected from the group comprising 6-chloro-3-indolyl-β-D-glucuronide and 5-bromo-6-chloro-3-indolyl-β-D-glucuronide.

16. The medium of claim 14, wherein said chromogenic arylsulfatase substrate is indoxyl-3-sulfate.

17. The medium of claim 14 further comprising at least one amine selected from the group consisting of glutamine, glutamic acid, tryptophan, phenylalanine, tyramine, octopamine, dopamine and norepinephrine.

18. The medium of claim 14, wherein said coordinating compound is selected from the group comprising manganese, copper and iron.

19. The medium of claim 14, wherein said gelling agent is selected from the group comprising alginates, gelatins, gellans and agar.

20. The medium of claim 14, wherein said casein-containing compound comprises a milk-derived preparation.

* * * * *